(12) United States Patent
Kitchens, II et al.

(10) Patent No.: US 10,140,534 B2
(45) Date of Patent: Nov. 27, 2018

(54) ULTRASONIC IMAGING DEVICES AND METHODS

(71) Applicant: QUALCOMM Incorporated, San Diego, CA (US)

(72) Inventors: Jack Conway Kitchens, II, Buffalo, NY (US); John Keith Schneider, Williamsville, NY (US); Stephen Michael Gojevic, Lockport, NY (US); Philip John Schneider, Williamsville, NY (US); Evan Michael Breloff, Lockport, NY (US); Ashish Hinger, Sunnyvale, CA (US); David William Burns, San Jose, CA (US); Muhammed Ibrahim Sezan, Los Gatos, CA (US)

(73) Assignee: QUALCOMM Incorporated, San Diego, CA (US)

( * ) Notice: Subject to any disclaimer, the term of this patent is extended or adjusted under 35 U.S.C. 154(b) by 133 days.

(21) Appl. No.: 15/253,387

(22) Filed: Aug. 31, 2016

(65) Prior Publication Data
US 2017/0090024 A1 Mar. 30, 2017

Related U.S. Application Data

(60) Provisional application No. 62/363,067, filed on Jul. 15, 2016, provisional application No. 62/233,335, filed on Sep. 26, 2015.

(51) Int. Cl.
*G06K 9/00* (2006.01)
*A61B 8/08* (2006.01)
(Continued)

(52) U.S. Cl.
CPC ........ *G06K 9/00885* (2013.01); *A61B 8/0858* (2013.01); *A61B 8/5223* (2013.01);
(Continued)

(58) Field of Classification Search
None
See application file for complete search history.

(56) References Cited

U.S. PATENT DOCUMENTS 5,515,298 A * 5/1996 Bicz .................... A61B 5/1172
600/437
5,689,576 A 11/1997 Schneider et al.
(Continued)

FOREIGN PATENT DOCUMENTS

WO 2015134816 A1 9/2015

OTHER PUBLICATIONS

Din M., "Data Acquisition System for Fingerprint Ultrasonic Imaging Device," Electronic Theses and Dissertations, 2011, 64 pages.
(Continued)

*Primary Examiner* — Hovhannes Baghdasaryan
(74) *Attorney, Agent, or Firm* — Weaver Austin Villeneuve & Sampson LLP

(57) ABSTRACT

An apparatus may include an ultrasonic sensor array and a control system. The control system may be configured to acquire first image data generated by the ultrasonic sensor array corresponding to at least one first reflected ultrasonic wave received by at least a portion of the ultrasonic sensor array from a target object during a first acquisition time window. The control system may be configured to acquire second image data generated by the ultrasonic sensor array corresponding to at least one second reflected ultrasonic wave received by at least a portion of the ultrasonic sensor array from the target object during a second acquisition time window that is longer than the first acquisition time window. The control system may further be configured to initiate an authentication process based on the first image data and the second image data.

41 Claims, 22 Drawing Sheets

(51) Int. Cl.
*A61B 8/00* (2006.01)
*G01S 7/52* (2006.01)
*G06K 9/20* (2006.01)
*A61B 5/1172* (2016.01)
*A61B 5/00* (2006.01)

(52) U.S. Cl.
CPC ............ *A61B 8/54* (2013.01); *G01S 7/52036* (2013.01); *G01S 7/52061* (2013.01); *G06K 9/0002* (2013.01); *G06K 9/2009* (2013.01); *A61B 5/1172* (2013.01); *A61B 5/6898* (2013.01); *G06K 2009/00932* (2013.01)

(56) References Cited

U.S. PATENT DOCUMENTS

| | | |
|---|---|---|
| 7,801,339 B2 | 9/2010 | Sidlauskas et al. |
| 8,977,013 B2 | 3/2015 | Maev et al. |
| 2005/0180620 A1 | 8/2005 | Takiguchi |
| 2011/0157346 A1* | 6/2011 | Zyzdryn ............ G06K 9/00046 |
| | | 348/77 |
| 2011/0279664 A1* | 11/2011 | Schneider ............ G06K 9/0002 |
| | | 348/77 |
| 2012/0068819 A1 | 3/2012 | McGrath et al. |
| 2012/0253154 A1 | 10/2012 | Phillips et al. |
| 2013/0123637 A1* | 5/2013 | Wohlschlager .......... A61B 8/02 |
| | | 600/453 |
| 2014/0049373 A1 | 2/2014 | Troy et al. |
| 2014/0219521 A1 | 8/2014 | Schmitt et al. |
| 2015/0015515 A1* | 1/2015 | Dickinson ............... G06F 3/043 |
| | | 345/173 |
| 2015/0198699 A1 | 7/2015 | Kuo et al. |
| 2016/0070967 A1 | 3/2016 | Du et al. |
| 2016/0350573 A1* | 12/2016 | Kitchens, II ......... G06K 9/0002 |

OTHER PUBLICATIONS

International Search Report and Written Opinion—PCT/US2016/053559—ISA/EPO—dated Apr. 11, 2017.
Partial International Search Report—PCT/US2016/053559—ISA/EPO—dated Jan. 2, 2017.

* cited by examiner

ULTRASONIC IMAGING DEVICES AND METHODS

PRIORITY CLAIM

This application claims benefit of and priority to: U.S. Provisional Patent Application No. 62/233,335, entitled "Methods and Systems for Detecting a Spoof" and filed on Sep. 26, 2015; and U.S. Provisional Patent Application No. 62/363,067, entitled "Spoof and Liveness Detection via Ultrasonic Imaging" and filed on Jul. 15, 2016, both of which are hereby incorporated by reference.

TECHNICAL FIELD

This disclosure relates generally to biometric devices and methods, including but not limited to ultrasonic sensor systems and methods for using such systems.

DESCRIPTION OF THE RELATED TECHNOLOGY

Technically savvy hackers revel in defeating the latest technical security innovations. For example, premium tier mobile phone manufacturers have had their first smartphones that incorporated fingerprint-based authentication systems successfully hacked shortly after product introduction. In some instances, spoofing may involve using a finger-like object that includes silicone rubber, polyvinyl acetate (white glue), gelatin, glycerin, etc., with a fingerprint pattern of a rightful user formed on an outside surface. In some cases, a hacker may form a fingerprint pattern of a rightful user on a sleeve or partial sleeve that can be slipped over or on the hacker's finger.

SUMMARY

The systems, methods and devices of the disclosure each have several innovative aspects, no single one of which is solely responsible for the desirable attributes disclosed herein.

One innovative aspect of the subject matter described in this disclosure may be implemented in an apparatus. The apparatus may include an ultrasonic sensor array and a control system that is configured for communication with the ultrasonic sensor array. In some examples, at least a portion of the control system may be coupled to the ultrasonic sensor array. In some implementations, a mobile device may be, or may include, the apparatus. For example, a mobile device may include an apparatus as disclosed herein.

The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. According to some examples, the control system may be configured to acquire first image data generated by the ultrasonic sensor array. The first image data may correspond to at least one first reflected ultrasonic wave received by at least a portion of the ultrasonic sensor array from a target object during a first acquisition time window. In some implementations, the control system may be configured to acquire second image data generated by the ultrasonic sensor array. The second image data may, in some examples, correspond to at least one second reflected ultrasonic wave received by at least a portion of the ultrasonic sensor array from the target object during a second acquisition time window that is longer than the first acquisition time window. According to some examples, the control system may be configured to initiate an authentication process based on the first image data and the second image data.

According to some examples, the first acquisition time window may be initiated at an end time of a first acquisition time delay. The second acquisition time window may, in some instances, be initiated at an end time of a second acquisition time delay. In some examples, the first acquisition time delay and the first acquisition time window may cause the first image data to correspond to a fingerprint feature of the target object. In some such examples, the second acquisition time delay and the second acquisition time window may cause the second image data to correspond to a sub-epidermal feature of the target object. In some implementations, the first acquisition time delay and the second acquisition time delay may be of equal duration. In some examples, the apparatus may include a platen positioned with respect to the ultrasonic sensor array. According to some implementations, the first acquisition time delay or the second acquisition time delay may correspond to an expected amount of time for an ultrasonic wave reflected from a surface of the platen to be received by the ultrasonic sensor array. According to some examples, the first acquisition time delay and the first acquisition time window may cause the first image data to correspond to a fingerprint feature of the target object. For example, the second acquisition time delay and the second acquisition time window may cause the second image data to correspond to a fingerprint feature of the target object and to a sub-epidermal feature of the target object.

In some instances, the target object may be a person's finger, such as a user's finger. According to some implementations, the first image data may include at least one fingerprint feature of the user's finger and the second image data may include at least one sub-epidermal feature of the user's finger. In some implementations, the first image data and the second image data may be acquired with a receiver bias control signal or a diode bias control signal.

According to some examples, the control system may be further configured to acquire third image data generated by the ultrasonic sensor array. The third image data may, for example, correspond to at least one third reflected ultrasonic wave received by at least a portion of the ultrasonic sensor array from the target object. In some instances, the initiated authentication process may be based on a temporal-based feature difference between the third image data and either the first image data or the second image data. According to some implementations, a liveness indicator may be generated based on the temporal-based feature difference.

In some implementations, the authentication process may involve detecting one or more surface fingerprint features on a surface of the target object and one or more subsurface fingerprint features below the surface of the target object. According to some implementations, the initiated authentication process may involve generating a spoof-detected indication based on differences between the surface fingerprint features and the subsurface fingerprint features.

In some examples, as part of the initiated authentication process, a fingerprint feature on a surface of the target object may be identified based on an enrolled fingerprint template. According to some examples, a plurality of image data may be acquired in a sub-surface region of the target object based on the identified fingerprint feature. In some such examples, the initiated authentication process may be further based on the plurality of image data acquired in the sub-surface region of the target object based on the identified fingerprint feature. In some implementations, the plurality of image data may be generated by at least a portion of the ultrasonic sensor array. According to some examples, a candidate user may be validated based, at least in part, on the presence or absence of temporal variations in the plurality of image data acquired in the sub-surface region.

Still other innovative aspects of the subject matter described in this disclosure can be implemented in an authentication method. The method may involve acquiring first image data generated by an ultrasonic sensor array. The first image data may, for example, correspond to at least one first reflected ultrasonic wave received by at least a portion of the ultrasonic sensor array from a target object during a first acquisition time window. The method may involve acquiring second image data generated by the ultrasonic sensor array. The second image data may, for example, correspond to at least one second reflected ultrasonic wave received by at least a portion of the ultrasonic sensor array from the target object during a second acquisition time window that is longer than the first acquisition time window. In some examples, the method may involve initiating an authentication process based on the first image data and the second image data.

In some examples, the first acquisition time window may be initiated at an end time of a first acquisition time delay and the second acquisition time window may be initiated at an end time of a second acquisition time delay. According to some implementations, the first acquisition time delay or the second acquisition time delay may correspond to an expected amount of time for an ultrasonic wave to be reflected from a surface of a platen and received by at least a portion of the ultrasonic sensor array. In some implementations, the first acquisition time delay and the first acquisition time window may cause the first image data to correspond to a fingerprint feature of the target object. In some such implementations, the second acquisition time delay and the second acquisition time window may cause the second image data to correspond to the fingerprint feature of the target object and to a sub-epidermal feature of the target object. In some instances, the first acquisition time delay and the second acquisition time delay may be of equal duration.

Some or all of the operations, functions and/or methods described herein may be performed by one or more devices according to instructions (e.g., software) stored on non-transitory media. Such non-transitory media may include memory devices such as those described herein, including but not limited to random access memory (RAM) devices, read-only memory (ROM) devices, etc. Accordingly, some innovative aspects of the subject matter described in this disclosure can be implemented in a non-transitory medium having software stored thereon.

For example, the software may include instructions for controlling one or more devices to perform an authentication method. In some examples, the method may involve acquiring first image data generated by an ultrasonic sensor array. The first image data may, for example, correspond to at least one first reflected ultrasonic wave received by at least a portion of the ultrasonic sensor array from a target object during a first acquisition time window. The method may involve acquiring second image data generated by the ultrasonic sensor array. The second image data may, for example, correspond to at least one second reflected ultrasonic wave received by at least a portion of the ultrasonic sensor array from the target object during a second acquisition time window that is longer than the first acquisition time window.

In some examples, the method may involve initiating an authentication process based, at least in part, on the first image data and the second image data.

In some examples, the first acquisition time window may be initiated at an end time of a first acquisition time delay and the second acquisition time window may be initiated at an end time of a second acquisition time delay. According to some implementations, the first acquisition time delay or the second acquisition time delay may correspond to an expected amount of time for an ultrasonic wave to be reflected from a surface of a platen and received by at least a portion of the ultrasonic sensor array. In some implementations, the first acquisition time delay and the first acquisition time window may cause the first image data to correspond to a fingerprint feature of the target object. In some such implementations, the second acquisition time delay and the second acquisition time window may cause the second image data to correspond to the fingerprint feature of the target object and to a sub-epidermal feature of the target object. In some instances, the first acquisition time delay and the second acquisition time delay may be of equal duration.

Other innovative aspects of the subject matter described in this disclosure can be implemented in an apparatus. The apparatus may include an ultrasonic sensor array and a control system that is configured for communication with the ultrasonic sensor array. In some examples, at least a portion of the control system may be coupled to the ultrasonic sensor array. In some implementations, a mobile device may be, or may include, the apparatus. For example, a mobile device may include an apparatus as disclosed herein.

The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. According to some examples, the control system may be configured to control the ultrasonic sensor array to acquire ultrasonic image data that corresponds to at least one reflected ultrasonic wave received by at least a portion of the ultrasonic sensor array from a target object during an acquisition time window. In some examples, the control system may be configured to extract first fingerprint data from the ultrasonic image data. According to some examples, the control system may be configured to determine whether the ultrasonic image data includes second fingerprint data at a depth that is different from the first fingerprint data and, if it is determined that the ultrasonic image data does not include second fingerprint data that is different from the first fingerprint data, perform an authentication process based, at least in part, on the first fingerprint data.

In some implementations, the control system may be further configured to determine sub-epidermal features from the ultrasonic image data. In some examples, the authentication process may be based, at least in part, on the sub-epidermal features. According to some implementations, the control system may be further configured to obtain first sub-epidermal features from first ultrasonic image data at a first time, to obtain second sub-epidermal features from second ultrasonic image data at a second time, and to make a liveness determination based on a change between the first sub-epidermal features and the second sub-epidermal features.

Still other innovative aspects of the subject matter described in this disclosure can be implemented in an authentication method. The method may involve controlling an ultrasonic sensor array to acquire ultrasonic image data that corresponds to at least one reflected ultrasonic wave received by at least a portion of the ultrasonic sensor array from a target object during an acquisition time window. In some examples, the method may involve extracting first fingerprint data from the ultrasonic image data, determining whether the ultrasonic image data includes second fingerprint data at a depth that is different from the first fingerprint data and, if it is determined that the ultrasonic image data does not include second fingerprint data that is different from the first fingerprint data, performing an authentication process based, at least in part, on the first fingerprint data.

In some examples, the method may involve determining sub-epidermal features from the ultrasonic image data. In some such examples, the authentication process may be based, at least in part, on the sub-epidermal features.

According to some implementations, the method may involve obtaining first sub-epidermal features from first ultrasonic image data at a first time, obtaining second sub-epidermal features from second ultrasonic image data at a second time and making a liveness determination based on a change between the first sub-epidermal features and the second sub-epidermal features.

Still other innovative aspects of the subject matter described in this disclosure can be implemented in a non-transitory medium having software stored thereon. For example, the software may include instructions for controlling one or more devices to perform an authentication method. In some examples, the method may involve controlling an ultrasonic sensor array to acquire ultrasonic image data that corresponds to at least one reflected ultrasonic wave received by at least a portion of the ultrasonic sensor array from a target object during an acquisition time window. In some examples, the method may involve extracting first fingerprint data from the ultrasonic image data, determining whether the ultrasonic image data includes second fingerprint data at a depth that is different from the first fingerprint data and, if it is determined that the ultrasonic image data does not include second fingerprint data that is different from the first fingerprint data, performing an authentication process based, at least in part, on the first fingerprint data.

In some examples, the method may involve determining sub-epidermal features from the ultrasonic image data. In some such examples, the authentication process may be based, at least in part, on the sub-epidermal features.

According to some implementations, the method may involve obtaining first sub-epidermal features from first ultrasonic image data at a first time, obtaining second sub-epidermal features from second ultrasonic image data at a second time and making a liveness determination based on a change between the first sub-epidermal features and the second sub-epidermal features.

BRIEF DESCRIPTION OF THE DRAWINGS

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale. Like reference numbers and designations in the various drawings indicate like elements.

DETAILED DESCRIPTION

The following description is directed to certain implementations for the purposes of describing the innovative aspects of this disclosure. However, a person having ordinary skill in the art will readily recognize that the teachings herein may be applied in a multitude of different ways. The described implementations may be implemented in any device, apparatus, or system that includes a biometric system as disclosed herein. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, etc., Bluetooth® devices, personal data assistants (PDAs), wireless electronic mail receivers, hand-held or portable computers, netbooks, notebooks, smartbooks, tablets, printers, copiers, scanners, facsimile devices, global positioning system (GPS) receivers/navigators, cameras, digital media players (such as MP3 players), camcorders, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, camera view displays (such as the display of a rear view camera in a vehicle), electronic photographs, electronic billboards or signs, projectors, architectural structures, microwaves, refrigerators, stereo systems, cassette recorders or players, DVD players, CD players, VCRs, radios, portable memory chips, washers, dryers, washer/dryers, parking meters, packaging (such as in electromechanical systems (EMS) applications including microelectromechanical systems (MEMS) applications, as well as non-EMS applications), aesthetic structures (such as display of images on a piece of jewelry or clothing) and a variety of EMS devices. The teachings herein also may be used in applications such as, but not limited to, electronic switching devices, radio frequency filters, sensors, accelerometers, gyroscopes, motion-sensing devices, magnetometers, inertial components for consumer electronics, parts of consumer electronics products, steering wheels or other automobile parts, varactors, liquid crystal devices, electrophoretic devices, drive schemes, manufacturing processes and electronic test equipment. Thus, the teachings are not intended to be limited to the implementations depicted solely in the Figures, but instead have wide applicability as will be readily apparent to one having ordinary skill in the art.

Figure 1A:
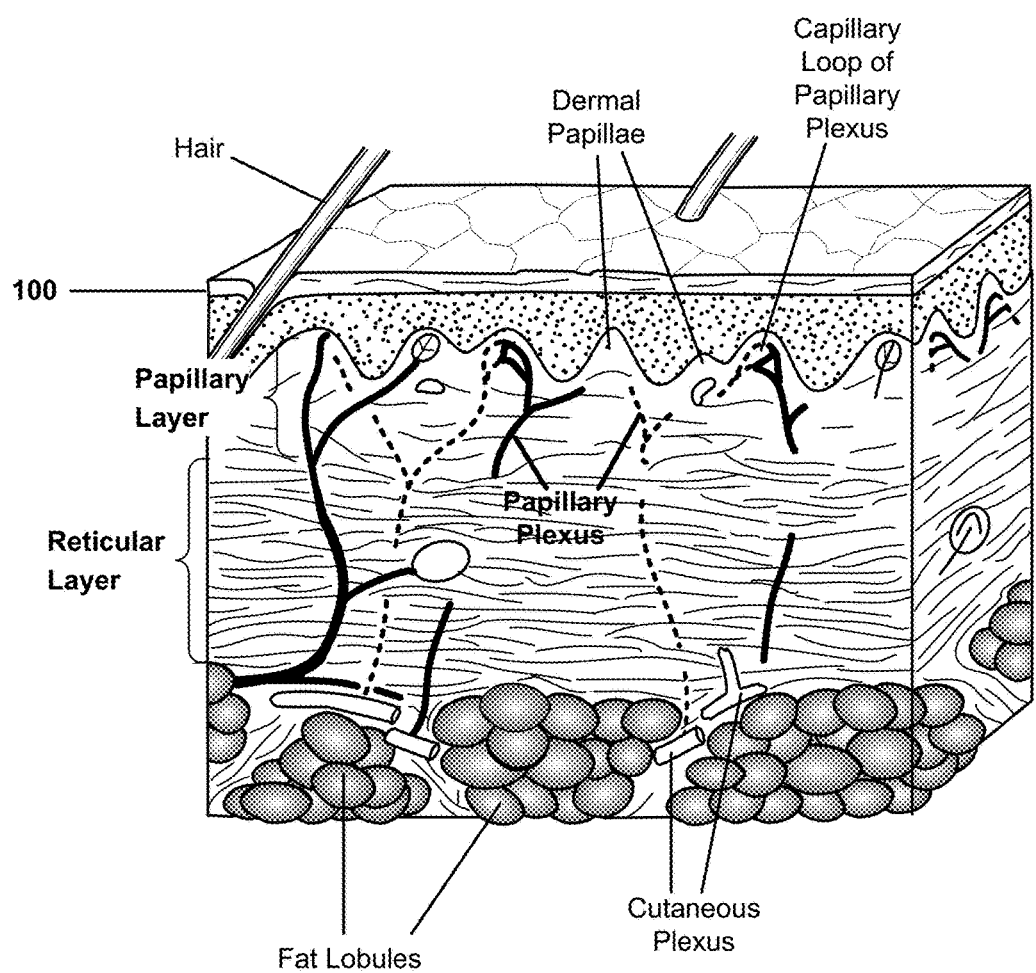
FIG. 1A shows examples of sub-epidermal features.

Some implementations may include an ultrasonic sensor system that is capable of obtaining image data from the epidermis, such as fingerprint image data, and image data that corresponds to sub-epidermal features. FIG. 1A shows examples of sub-epidermal features. As used herein, the term "sub-epidermal features" may refer to any of the tissue layers that underlie the epidermis 100, including the dermis, the papillary layer, the reticular layer, the subcutis, etc., and any blood vessels, lymph vessels, sweat glands, hair follicles, hair papilla, fat lobules, etc., that may be present within such tissue layers. Accordingly, sub-epidermal features also may include features not shown in FIG. 1A, such as muscle tissue, bone material, etc.

Some implementations may be capable of performing enrollment and authentication processes that are based, at least in part, on sub-epidermal features. Some such processes also may be based on fingerprint image data, or on fingerprint minutiae or fingerprint image features such as keypoints derived from fingerprint image data. The authentication processes may involve spoof detection and/or liveness detection.

In some examples, the user authentication process may involve comparing "attribute information" obtained from received image data, based on the signals from an ultrasonic sensor array, with stored attribute information obtained from image data that has previously been received from an authorized user during an enrollment process. According to some such examples, the attribute information may include information regarding sub-epidermal features, such as information regarding features of the dermis, features of the subcutis, blood vessel features, lymph vessel features, sweat gland features, hair follicle features, hair papilla features and/or fat lobule features, along with minutiae or keypoint information associated with an enrolled fingerprint.

Alternatively, or additionally, in some implementations the attribute information obtained from the received image data and the stored attribute information may include information regarding bone tissue features, muscle tissue features and/or epidermal or sub-epidermal tissue features. For example, according to some implementations, the user authentication process may involve obtaining fingerprint image data and sub-epidermal image data. In such examples, the authentication process may involve evaluating attribute information obtained from the fingerprint image data.

The attribute information obtained from the received image data and the stored attribute information that are compared during an authentication process may include biometric template data corresponding to the received image data and biometric template data corresponding to the stored image data. One well-known type of biometric template data is fingerprint template data, which may indicate types and locations of fingerprint minutia or keypoints. A user authentication process based on attributes of fingerprint image data may involve comparing received and stored fingerprint template data. Such a process may or may not involve directly comparing received and stored fingerprint image data.

Similarly, biometric template data corresponding to sub-epidermal features may include information regarding the attributes of blood vessels, such as information regarding the types and locations of blood vessel features, such as blood vessel size, blood vessel orientation, the locations of blood vessel branch points, etc. Alternatively, or additionally, biometric template data corresponding to sub-epidermal features may include attribute information regarding the types (e.g., the sizes, shapes, orientations, etc.) and locations of features of the dermis, features of the subcutis, lymph vessel features, sweat gland features, hair follicle features, hair papilla features, fat lobule features, muscle tissue and/or bone material.

Particular implementations of the subject matter described in this disclosure may be implemented to realize one or more of the following potential advantages. As noted above, some spoofing techniques are based on forming fingerprint-like features on an object, which may be a finger-like object. However, making a finger-like object with detailed sub-epidermal features, muscle tissue features and/or bone tissue features would be challenging and expensive. Making such features accurately correspond with those of an authorized user would be even more challenging. Making such features moveable in a human-like biomimicry manner or in a manner replicating a rightful user raises the bar even higher for spoof fabrication. Because some disclosed implementations involve obtaining attribute information that is based, at least in part, on sub-epidermal features, some such implementations may provide more reliable authentication. Some such implementations may be capable of providing determinations of "liveness."

Figure 1B:
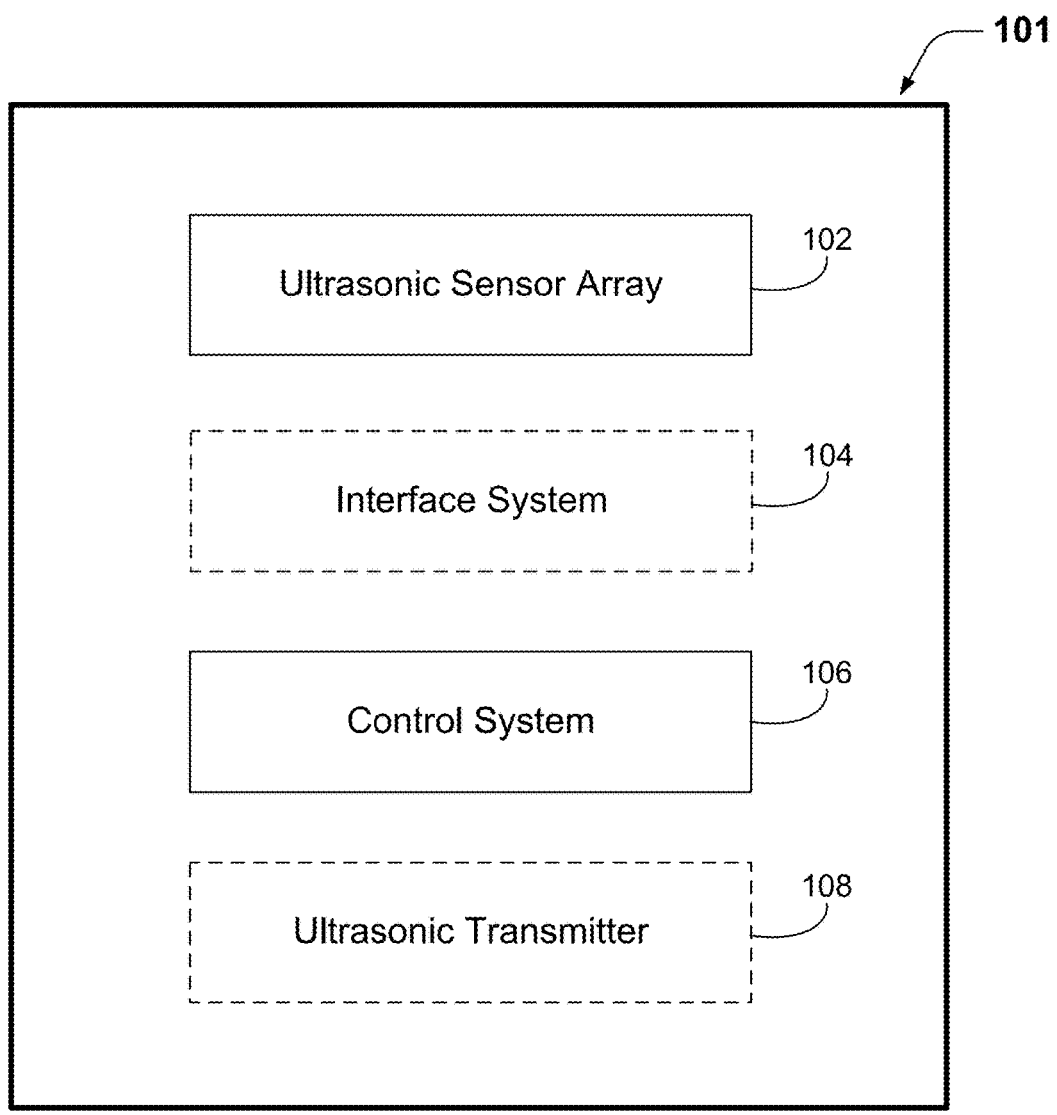
FIG. 1B is a block diagram that shows example components of an apparatus according to some disclosed implementations.

FIG. 1B is a block diagram that shows example components of an apparatus according to some disclosed implementations. In this example, the apparatus 101 includes an ultrasonic sensor array 102 and a control system 106. Although not shown in FIG. 1B, the apparatus 101 may include a substrate. Some examples are described below. Some implementations of the apparatus 101 may include an interface system 104. In some examples, the apparatus 101 may include an ultrasonic transmitter 108.

Various examples of ultrasonic sensor arrays 102 are disclosed herein, some of which may include a separate ultrasonic transmitter and some of which may not. Although shown as separate elements in FIG. 1B, in some implementations the ultrasonic sensor array 102 and the ultrasonic transmitter 108 may be combined in an ultrasonic transceiver. For example, in some implementations, the ultrasonic sensor array 102 may include a piezoelectric receiver layer, such as a layer of PVDF polymer or a layer of PVDF-TrFE copolymer. In some implementations, a separate piezoelectric layer may serve as the ultrasonic transmitter. In some implementations, a single piezoelectric layer may serve as the transmitter and as a receiver. In some implementations, other piezoelectric materials may be used in the piezoelectric layer, such as aluminum nitride (AlN) or lead zirconate titanate (PZT). The ultrasonic sensor array 102 may, in some examples, include an array of ultrasonic transducer elements, such as an array of piezoelectric micromachined ultrasonic transducers (PMUTs), an array of capacitive micromachined ultrasonic transducers (CMUTs), etc. In some such examples, a piezoelectric receiver layer, PMUT elements in a single-layer array of PMUTs, or CMUT elements in a single-layer array of CMUTs, may be used as ultrasonic transmitters as well as ultrasonic receivers. According to some alternative examples, the ultrasonic sensor array 102 may be an ultrasonic receiver array and the ultrasonic transmitter 108 may include one or more separate elements. In some such examples, the ultrasonic transmitter 108 may include an ultrasonic plane-wave generator, such as those described below.

The control system 106 may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system 106 also may include (and/or be configured for communication with) one or more memory devices, such as one or more random access memory (RAM) devices, read-only memory (ROM) devices, etc. Accordingly, the apparatus 101 may have a memory system that includes one or more memory devices, though the memory system is not shown in FIG. 1B. The control system 106 may be capable of receiving and processing data from the ultrasonic sensor array 102, e.g., as described below. If the apparatus 101 includes an ultrasonic transmitter 108, the control system 106 may be capable of controlling the ultrasonic transmitter 108, e.g., as disclosed elsewhere herein. In some implementations, functionality of the control system 106 may be partitioned between one or more controllers or processors, such as a dedicated sensor controller and an applications processor of a mobile device.

Some implementations of the apparatus 101 may include an interface system 104. In some examples, the interface system may include a wireless interface system. In some implementations, the interface system may include a user interface system, one or more network interfaces, one or more interfaces between the control system 106 and a memory system and/or one or more interfaces between the control system 106 and one or more external device interfaces (e.g., ports or applications processors).

The interface system 104 may be configured to provide communication (which may include wired or wireless communication, such as electrical communication, radio communication, etc.) between components of the apparatus 101. In some such examples, the interface system 104 may be configured to provide communication between the control system 106 and the ultrasonic sensor array 102. According to some such examples, a portion of the interface system 104 may couple at least a portion of the control system 106 to the ultrasonic sensor array 102, e.g., via electrically conducting material. If the apparatus 101 includes an ultrasonic transmitter 108 that is separate from the ultrasonic sensor array 102, the interface system 104 may be configured to provide communication between at least a portion of the control system 106 and the ultrasonic transmitter 108. According to some examples, the interface system 104 may be configured to provide communication between the system and other devices and/or human beings. In some such examples, the interface system 104 may include one or more user interfaces. The interface system 104 may, in some examples, include one or more network interfaces and/or one or more external device interfaces (such as one or more universal serial bus (USB) interfaces). In some implementations, the apparatus 101 may include a memory system. The interface system 104 may, in some examples, include at least one interface between the control system 106 and a memory system.

The apparatus 101 may be used in a variety of different contexts, many examples of which are disclosed herein. For example, in some implementations a mobile device may include at least a portion of the apparatus 101. In some implementations, a wearable device may include at least a portion of the apparatus 101. The wearable device may, for example, be a bracelet, an armband, a wristband, a ring, a headband or a patch. In some implementations, the control system 106 may reside in more than one device. For example, a portion of the control system 106 may reside in a wearable device and another portion of the control system 106 may reside in another device, such as a mobile device (e.g., a smartphone or a tablet computer). The interface system 104 also may, in some such examples, reside in more than one device.

Figure 1C:
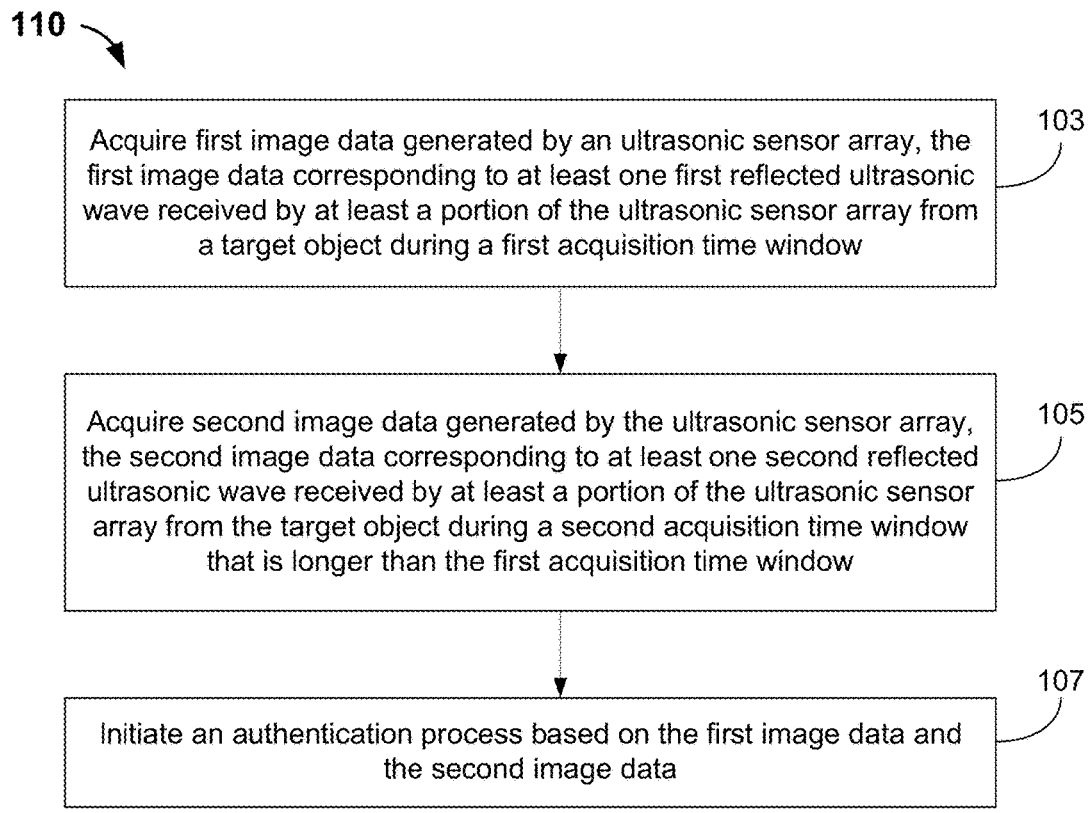
FIG. 1C is a flow diagram that provides examples of biometric system operations.

FIG. 1C is a flow diagram that provides examples of biometric system operations. The blocks of FIG. 1C (and those of other flow diagrams provided herein) may, for example, be performed by the apparatus 101 of FIG. 1B or by a similar apparatus. As with other methods disclosed herein, the method outlined in FIG. 1C may include more or fewer blocks than indicated. Moreover, the blocks of methods disclosed herein are not necessarily performed in the order indicated.

In this example, block 103 involves acquiring first image data generated by an ultrasonic sensor array, such as the ultrasonic sensor array 102 of FIG. 1B. In some examples, the first image data may be received from the ultrasonic sensor array, whereas in other examples the first image data may be received from a memory device, such as a buffer. In this instance, the first image data corresponds to at least one first reflected ultrasonic wave received by at least a portion of the ultrasonic sensor array from a target object during a first acquisition time window. The target object may, in some examples, be a person's finger, such as a user's finger. However, in other examples the target object may be an artificial finger-like object, which may be referred to as a "fake finger." Data received from an ultrasonic sensor array may be referred to herein as "image data," although the image data will generally be received in the form of electrical signals. Accordingly, without additional processing such image data would not necessarily be perceivable by a human being as an image.

According to this implementation, block 105 involves acquiring second image data generated by the ultrasonic sensor array. In this example, the second image data corresponds to at least one second reflected ultrasonic wave received by at least a portion of the ultrasonic sensor array from at least the portion of the target object during a second acquisition time window that is longer than the first acquisition time window. According to some implementations, the first image data may include at least one fingerprint feature of the target object and the second image data may include at least one sub-epidermal feature of the target object. In some implementations, the first image data and the second image data may be acquired with a receiver bias control signal or a diode bias control signal. Some examples are described below.

According to this example, block 107 involves initiating an authentication process based on the first image data and the second image data. Various examples of authentication processes are disclosed herein. In some instances, the authentication process may validate a rightful user. In some such examples, the target object may be a finger of the rightful user.

According to some examples, the control system may be further configured to acquire third image data generated by the ultrasonic sensor array. The third image data may, for example, correspond to at least one third reflected ultrasonic wave received by at least a portion of the ultrasonic sensor array from at least the portion of the target object. In some instances, the initiated authentication process may be based, at least in part, on temporal changes in the sizes, arrangements or other aspects of features indicated by the first, second and/or third image data. If the first, second and third image data are obtained at different times, such changes may, for example, be detected by comparing feature sizes, arrangements, etc., indicated by the third image data with feature sizes, arrangements, etc., indicated by the first image data and/or the second image data. A temporal change of this type may be referred to herein as a "temporal-based feature difference." According to some implementations, a liveness indicator may be generated based on the temporal-based feature difference. Some examples are described below with reference to FIGS. 3B and 6A-6C.

In some implementations, the authentication process may involve determining whether there are fingerprint features on, or near, a surface of the target object and fingerprint features below the surface of the target object. According to some implementations, a spoof-detected indication may be generated based, at least in part, on differences between the fingerprint features on the surface of the target object and the fingerprint features below the surface of the target object. In some examples, the spoof-detected indication may be an alert, such as a text-based message, that is transmitted to another device and/or saved in memory. According to some implementations, in response to a spoof-detected indication, a control system may be configured to store the first image data, the second image data, the third image data, fingerprint minutiae, fingerprint keypoints or fingerprint features if surface fingerprint features on the surface of the target object and subsurface fingerprint features below the surface of the target object are detected. In this manner, information regarding the fingerprints of a hacker may be saved for future use. Some examples are described below.

Figure 4:
FIG. 4 shows an example of an image of a fingerprint superimposed on multiple sub-epidermal features.

In some examples, a fingerprint feature on a surface of the target object may be identified based on an enrolled fingerprint template. According to some examples, a plurality of image data may be acquired in a sub-surface region of the target object based on the identified fingerprint feature. One example is shown in FIG. 4 and is described below. In some such examples, the authentication process may be further based on the plurality of image data acquired in the sub-surface region. In some implementations, the plurality of image data may be acquired from a portion of the ultrasonic sensor array. In some examples, a candidate user may be evaluated based, at least in part, on temporal or non-temporal variations in the plurality of image data acquired in the sub-surface region. According to some examples, a rightful user may be validated based on temporal or non-temporal variations in the plurality of image data acquired in the sub-surface region.

According to some examples, the first acquisition time window may be initiated at an end time of a first acquisition time delay. The second acquisition time window may, in some instances, be initiated at an end time of a second acquisition time delay. In some examples, the first acquisition time delay and the first acquisition time window may cause at least a portion of the first image data to correspond to a fingerprint feature of the target object. In some instances, the target object may be a person's finger, such as a user's finger. In some such examples, the second acquisition time delay and the second acquisition time window may cause at least a portion of the second image data to correspond to a sub-epidermal feature of the user's finger.

Figure 1D:
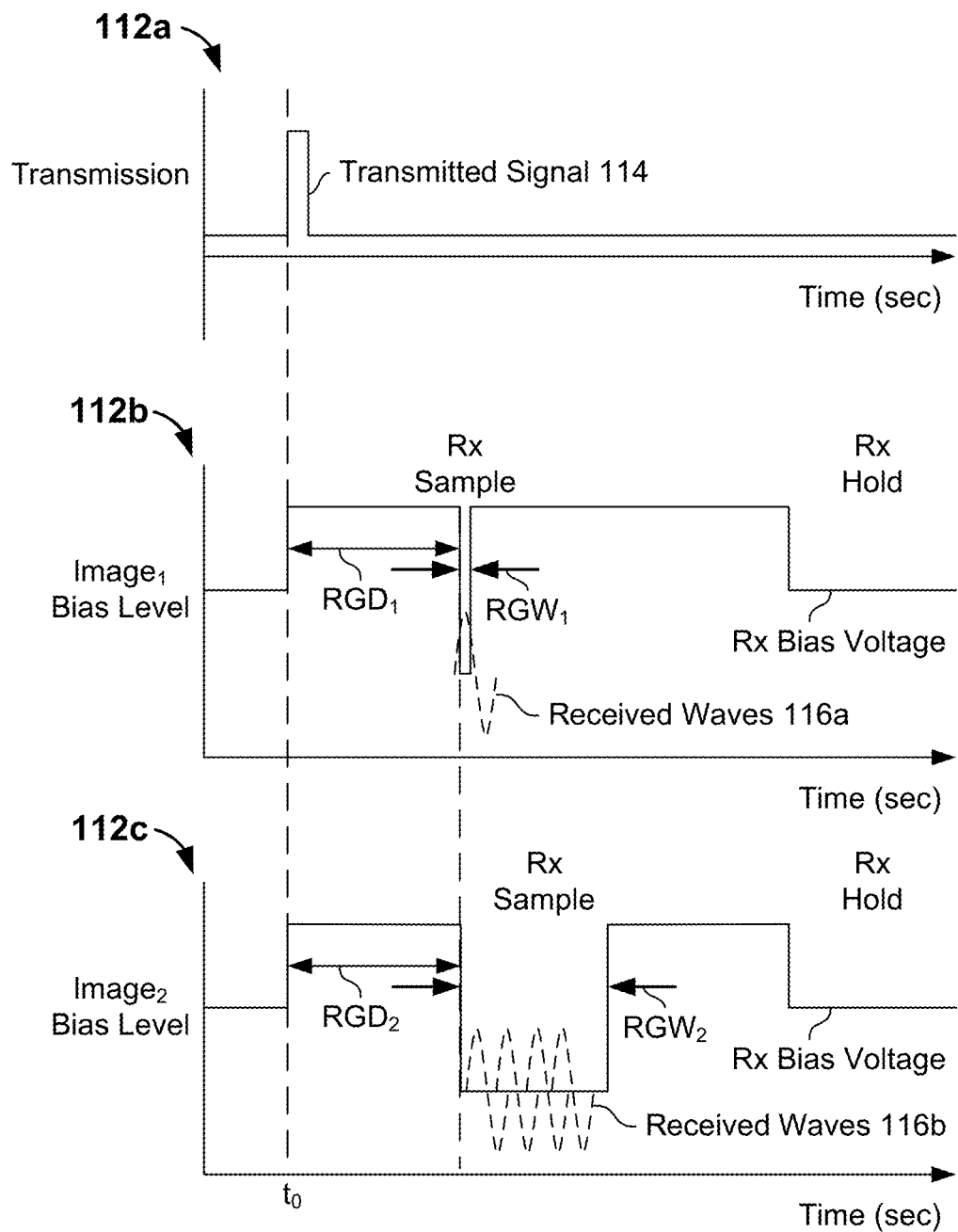
FIG. 1D shows some examples of acquisition time delays and acquisition time windows.

FIG. 1D shows some examples of acquisition time delays and acquisition time windows. In FIG. 1D, an acquisition time delay is labeled as "RGD," an acronym for "range-gate delay," and an acquisition time window is labeled as "RGW," an acronym for "range-gate window." Graph 112$a$ shows a transmitted signal 114 that is initiated at a time $t_0$. The transmitted signal 114 may, for example, be a pulse of ultrasound. In alternative examples, multiple pulses of ultrasound may be transmitted.

Graph 112$b$ shows examples of a first acquisition time delay $RGD_1$ and a first acquisition time window $RGW_1$. The received waves 116$a$ represent reflected waves that are received by an ultrasonic sensor array and sampled during the first acquisition time window $RGW_1$, after the first acquisition time delay $RGD_1$. In some examples, the acquisition time delay may be in the range of about 10 nanoseconds to about 20,000 nanoseconds or more. In some implementations, the first acquisition time window may be in the range of 5 to 50 nanoseconds, or in the range of approximately 5 to 50 nanoseconds. In some examples, "approximately" or "about" may mean within +/−5%, whereas in other examples "approximately" or "about" may mean within +/−10%, +/−15% or +/−20%. However, in some implementations the first acquisition time window may be in the range of 50 to 20,000 nanoseconds, or in the range of approximately 50 to 20,000 nanoseconds or more. According to some examples, the apparatus 101 may include a platen. The platen may be positioned with respect to the ultrasonic sensor array 102. For example, the platen may be positioned proximate the ultrasonic sensor array 102 and/or attached to the ultrasonic sensor array 102. In some such examples, the first acquisition time delay may correspond to an expected amount of time for an ultrasonic wave reflected from a surface of the platen to be received by at least a portion of the ultrasonic sensor array 102. Accordingly, the first acquisition time delay and the first acquisition time window may be selected to capture one or more fingerprint features of a target object placed on a surface of a platen. For example, in some implementations with a platen about 400 microns thick, the acquisition time delay (RGD) may be set to about 1,000 nanoseconds and the acquisition time window (RGW) may be set to about 50 nanoseconds.

Graph 112$c$ shows examples of a second acquisition time delay $RGD_2$ and a second acquisition time window $RGW_2$. The received waves 116$b$ represent reflected waves that are received by an ultrasonic sensor array and sampled during the second acquisition time window $RGW_2$, after the second acquisition time delay $RGD_2$. In this example, the first acquisition time delay equals the second acquisition time delay. However, in other implementations, the first acquisition time delay may not equal the second acquisition time delay. In this example, the first acquisition time delay and the second acquisition time delay are both measured from the time $t_0$. However, in other implementations, the first acquisition time delay and the second acquisition time delay may be measured from a different initial time. In some examples, the first acquisition time delay and/or the second acquisition time delay may correspond to a time required for a transmitted ultrasonic wave to be reflected from a surface of a platen and received by at least a portion of the ultrasonic sensor array.

Figures 2A, 2B, 2C:
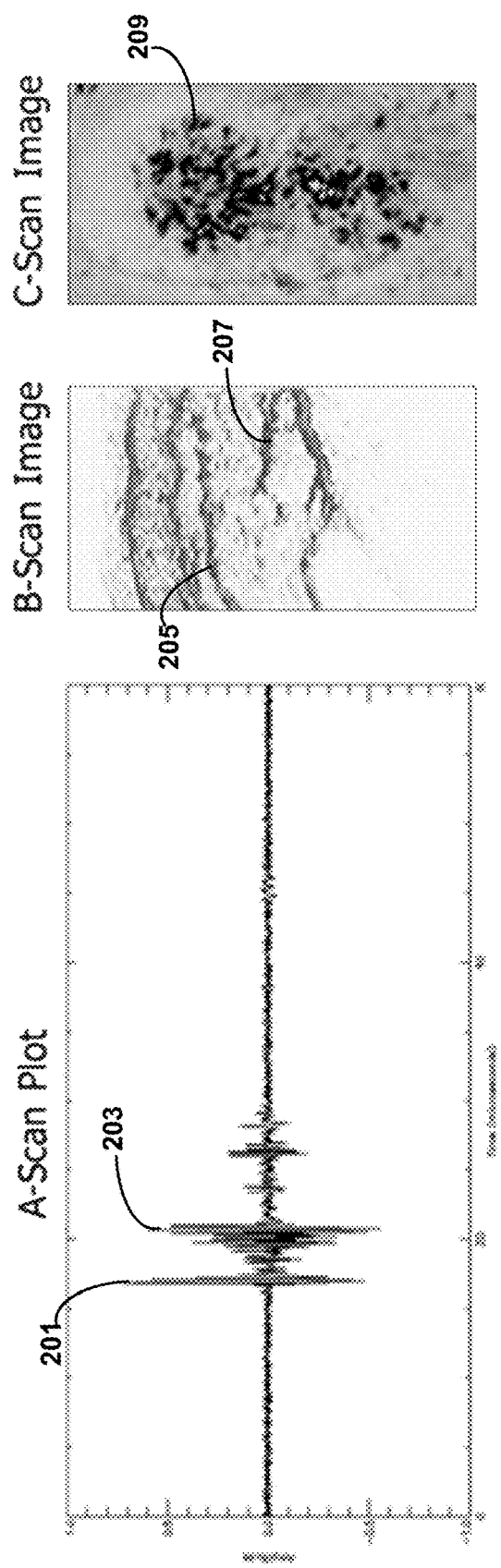
FIGS. 2A-2C show examples of A-scan, B-scan and C-scan images.

According to some implementations, the second acquisition time window may be in the range of 5 to 50 nanoseconds, or in the range of approximately 5 to 50 nanoseconds. However, in some implementations the second acquisition time window may be in the range of 50 to 2,000 nanoseconds, or in the range of approximately 50 to 2,000 nanoseconds. In some examples the second acquisition time window may be in the range of 2,000 to 20,000 nanoseconds, or in the range of approximately 2,000 to 20,000 nanoseconds or more. In some examples, the second acquisition time delay and the second acquisition time window may be selected to capture to a fingerprint feature of the target object and a sub-epidermal feature of the target object. For example, in some implementations with a platen about 400 microns thick, the acquisition time delay (RGD) may be set to about 1,000 nanoseconds and the acquisition time window (RGW) may be set to about 1,000 nanoseconds FIGS. 2A-2C show examples of A-scan, B-scan and C-scan images. As shown in FIG. 2A, an A-scan plot of reflection amplitude versus time may be obtained from a single ultrasonic receiver or transceiver, such as a sensor pixel or a small group of sensor pixels. The high-amplitude events shown in FIG. 2A indicate reflections from within a target object, such as a finger, caused by acoustic impedance contrast within the target object. The surface of a bone, for example, generally has a relatively high acoustic impedance contrast with the overlying tissue and therefore produces a relatively high-amplitude reflection. The presence of multiple reflections in an A-scan, such as the reflections 201 and 203 shown in FIG. 2A, indicates that the target object is not, for example, air or a solid piece of silicone rubber or other such material that may be used for spoofing. The presence of such reflections, in conjunction with a fingerprint match, would suggest that the target object is actually a finger of an authorized user. However, a fake finger could be made with multiple layers having different acoustic impedances. Moreover, a fingerprint pattern of a rightful user on a sleeve slipped over or placed on a hacker's finger could defeat such a simple anti-spoofing method.

A B-scan image, such as that shown in FIG. 2B, may be obtained from a single row or column of ultrasonic receivers or transceivers. In this example, travel time is along the vertical axis of the B-scan image. Various reflections, including reflections 205 and 207, may be seen in the B-scan image of FIG. 2B. The reflections 205 and 207 correspond to sub-epidermal features of a finger in this example. The presence of such complex features provides a stronger indication that the target object is actually a finger, as compared with A-scan image data.

A C-scan image may be obtained from an array of ultrasonic receivers or transceivers, such as a grid of ultrasonic receivers or transceivers or a focused single-element transceiver with arcuate and translational mechanical motion capability. In the example shown in FIG. 2C, ultrasonic image data has been obtained at a depth suitable for obtaining a 2-D C-scan image of sub-epidermal features, such as the feature 209 that corresponds to a region of elevated acoustic impedance contrast, such as sub-epidermal vasculature or aggregates of fatty tissue. The depth may correspond with a selected time interval between the time ultrasound is transmitted and the time during which reflected ultrasonic waves are sampled (which may be referred to herein as the acquisition time delay or the range-gate delay (RGD)). For example, a relatively larger range-gate delay may be selected to receive reflected ultrasonic waves primarily from bones and a relatively smaller range-gate delay may be selected to receive reflected ultrasonic waves primarily from ridges and valleys of a fingerprint or sub-epidermal features such as blood vessels, blood, muscle tissue features or bone tissue features.

The amount of detail in the C-scan image provides yet stronger indications that the target object is actually a finger. Moreover, sub-epidermal features are indicated in sufficient detail such that their corresponding attribute information may be used as part of an authentication process such as those described below, such as distinctive C-scan features referenced in depth and offset with respect to one or more fingerprint minutiae of a rightful user's finger.

Figure 2D:
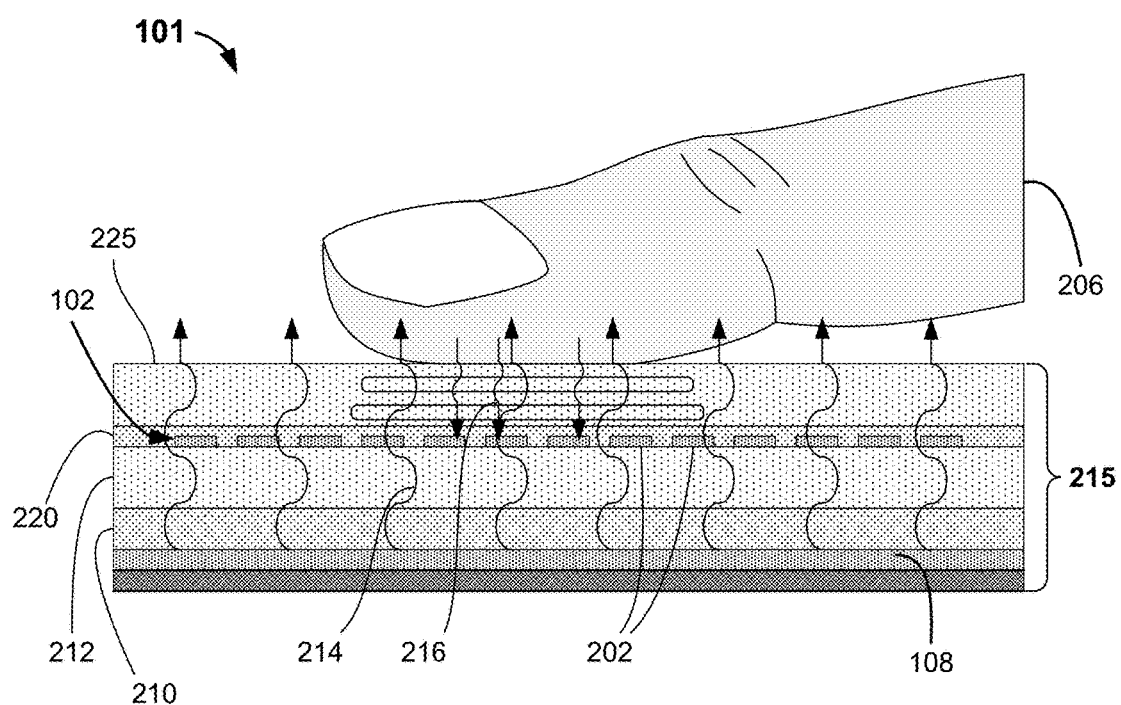
FIG. 2D shows an example of a cross-sectional view of an apparatus capable of performing at least some methods that are described herein.

FIG. 2D shows an example of a cross-sectional view of an apparatus capable of performing at least some methods that are described herein. For example, the apparatus 101 may be capable of performing the methods that are described herein with reference to FIGS. 1C and 3A. The apparatus 101 is an example of a device that may be included in a biometric system such as those disclosed herein. Here, the apparatus 101 is an example of the apparatus 101 that is described above with reference to FIG. 1B. As with other implementations shown and described herein, the types of elements, the arrangement of the elements and the dimensions of the elements illustrated in FIG. 2D are merely shown by way of example.

FIG. 2D shows an example of ultrasonic waves reflecting from a target object. In this example, the target object is a finger 206 being insonified by transmitted ultrasonic waves 214. In this example, the transmitted ultrasonic waves 214 are instances of the transmitted signal 114 that is described above with reference to FIG. 1D. Here, the reflected ultrasonic waves 216 that are received by at least a portion of the ultrasonic sensor array 102 are instances of the received waves 116a and 116b that are shown in FIG. 1D. However, other implementations may involve different types of transmitted ultrasonic waves 214 and/or reflected ultrasonic waves 216, including but not limited to the examples shown in FIGS. 3B and 13, which are described below.

In this example, the ultrasonic waves are transmitted by an ultrasonic transmitter 108 that is separate from the ultrasonic sensor array 102. In the example shown in FIG. 2D, at least a portion of the apparatus 101 includes an ultrasonic transmitter 108 that may function as a plane-wave ultrasonic transmitter. In some implementations, the ultrasonic transmitter 108 may include a piezoelectric transmitter layer with transmitter excitation electrodes disposed on each side of the piezoelectric transmitter layer.

In this example, the ultrasonic sensor array 102 may function as an ultrasonic receiver array. In some such examples, the ultrasonic sensor array 102 may include an array of pixel input electrodes and sensor pixels formed in part from TFT circuitry, an overlying piezoelectric receiver layer 220 of piezoelectric material such as PVDF or PVDF-TrFE, and an upper electrode layer positioned on the piezoelectric receiver layer, which will sometimes be referred to herein as a receiver bias electrode. Examples of suitable ultrasonic transmitters and ultrasonic receiver arrays are described below with reference to FIGS. 15A and 15B.

However, in alternative implementations, the ultrasonic sensor array 102 and the ultrasonic transmitter 108 may be combined in an ultrasonic transceiver array. For example, in some implementations, the ultrasonic sensor array 102 may include a piezoelectric receiver layer, such as a layer of PVDF polymer or a layer of PVDF-TrFE copolymer. In some implementations, a separate piezoelectric layer may serve as the ultrasonic transmitter. In some examples, a single piezoelectric layer may serve as the transmitter and as a receiver. In some implementations, other piezoelectric materials may be used in the piezoelectric layer, such as aluminum nitride (AlN) or lead zirconate titanate (PZT). The ultrasonic sensor array 102 may, in some examples, include an array of ultrasonic transducer elements, such as an array of piezoelectric micromachined ultrasonic transducers (PMUTs), an array of capacitive micromachined ultrasonic transducers (CMUTs), etc. In some such examples, a piezoelectric receiver layer, PMUT elements in a single-layer array of PMUTs, or CMUT elements in a single-layer array of CMUTs, may be used as ultrasonic transmitters as well as ultrasonic receivers.

In this example, the transmitted ultrasonic waves 214 have been transmitted from the ultrasonic transmitter 108 through a sensor stack 215 and into an overlying finger 206. The various layers of the sensor stack 215 may, in some examples, include one or more substrates of glass or other material (such as plastic or sapphire) that is substantially transparent to visible light. In this example, the sensor stack 215 includes a substrate 210 to which a light source system (not shown) is coupled, which may be a backlight of a display according to some implementations. In alternative implementations, a light source system may be coupled to a front light. Accordingly, in some implementations a light source system may be configured for illuminating a display and the target object.

In this implementation, the substrate 210 is coupled to a thin-film transistor (TFT) substrate 212 for the ultrasonic sensor array 102. According to this example, a piezoelectric receiver layer 220 overlies the sensor pixels 202 of the ultrasonic sensor array 102 and a platen 225 overlies the piezoelectric receiver layer 220. Accordingly, in this example the apparatus 101 is capable of transmitting the ultrasonic waves 214 through one or more substrates of the sensor stack 215 that include the ultrasonic sensor array 102 with substrate 212 and the platen 225 that may also be viewed as a substrate. In some implementations, sensor pixels 202 of the ultrasonic sensor array 102 may be transparent, partially transparent or substantially transparent, such that the apparatus 101 may be capable of transmitting light from a light source system through elements of the ultrasonic sensor array 102. In some implementations, the ultrasonic sensor array 102 and associated circuitry may be formed on or in a glass, plastic or silicon substrate.

Figure 2E:
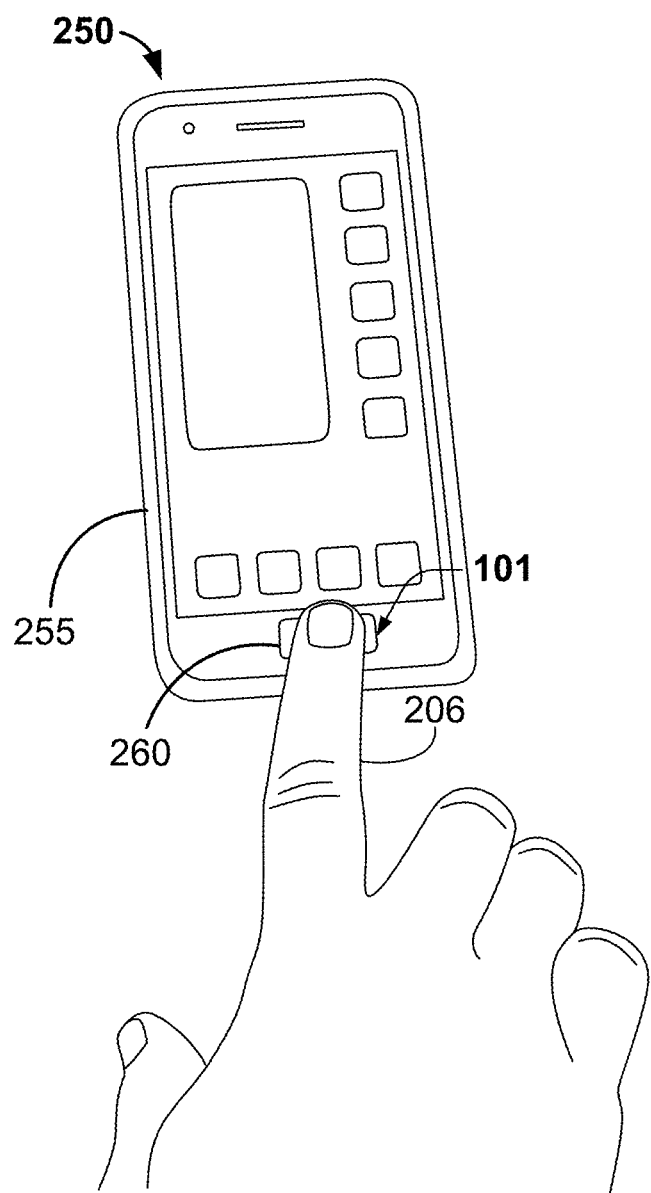
FIG. 2E shows an example of a mobile device that includes a biometric system as disclosed herein.

FIG. 2E shows an example of a mobile device that includes a biometric system as disclosed herein. In this example, the mobile device 250 is a smartphone. However, in alternative examples the mobile device 250 may another type of mobile device, such as a mobile health device, such as a mobile drug delivery device, a wearable device, a tablet computer, etc.

In this example, the mobile device 250 includes an instance of the apparatus 101 that is described above with reference to FIG. 1B. In this example, the apparatus 101 is disposed, at least in part, within the mobile device enclosure 255. According to this example, at least a portion of the apparatus 101 is located in the portion of the mobile device 250 that is shown being touched by the finger 206, which corresponds to the location of button 260. Accordingly, the button 260 may be an ultrasonic button. In some implementations, the button 260 may serve as a home button. In some implementations, the button 260 may serve as an ultrasonic authenticating button, with the ability to turn on or otherwise wake up the mobile device 250 when touched or pressed and/or to authenticate or otherwise validate a user when applications running on the mobile device (such as a wake-up function) warrant such a function.

In this implementation, the mobile device 250 may be capable of performing a user authentication process. For example, a control system of the mobile device 250 may be capable of comparing attribute information obtained from image data received via an ultrasonic sensor array of the apparatus 101 with stored attribute information obtained from image data that has previously been received from an authorized user. In some examples, the attribute information obtained from the received image data and the stored attribute information may include attribute information corresponding to at least one of sub-epidermal features, muscle tissue features or bone tissue features.

According to some implementations, the attribute information obtained from the received image data and the stored attribute information may include information regarding fingerprint minutia or keypoints. In some such implementations, the user authentication process may involve evaluating information regarding the fingerprint minutia as well as at least one other type of attribute information, such as attribute information corresponding to sub-epidermal features. According to some such examples, the user authentication process may involve evaluating information regarding the fingerprint minutia or keypoints as well as attribute information corresponding to vascular features. For example, attribute information obtained from a received image of blood vessels in the finger may be compared with a stored image of blood vessels in the authorized user's finger 206.

Figure 3A:
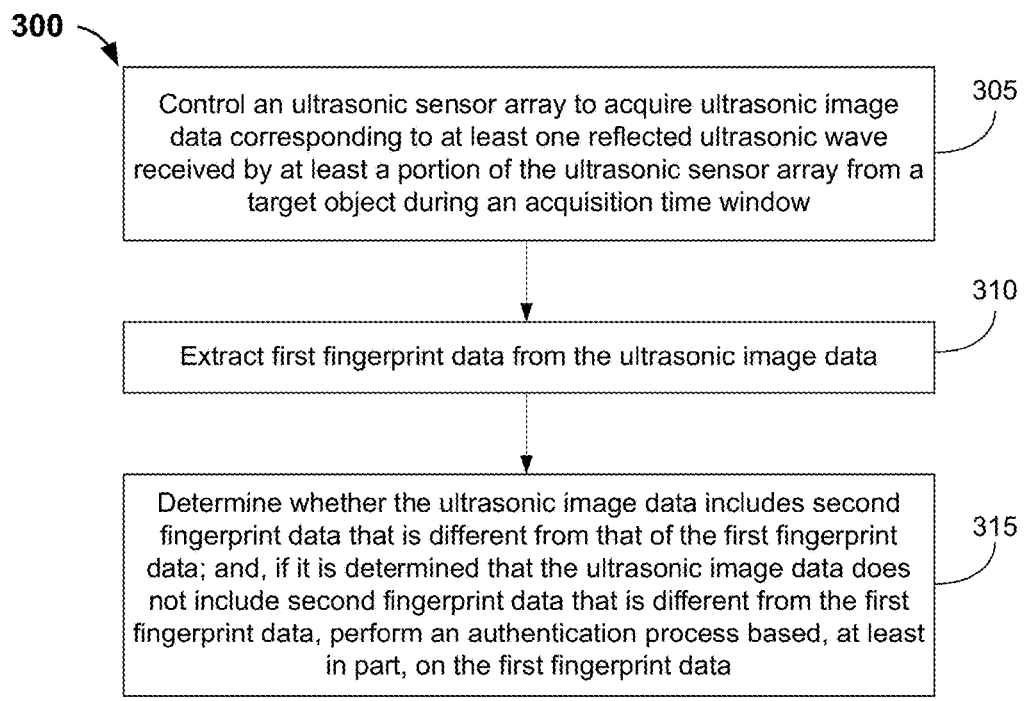
FIG. 3A is a flow diagram that includes blocks of an alternative method.

FIG. 3A is a flow diagram that includes blocks of an alternative method. The blocks of FIG. 3A (and those of other flow diagrams provided herein) may, for example, be performed by the apparatus 101 of any one of FIG. 1B, 2D or 2E, or by a similar apparatus. As with other methods disclosed herein, the method outlined in FIG. 3A may include more or fewer blocks than indicated. Moreover, the blocks of methods disclosed herein are not necessarily performed in the order indicated.

In this example, block 305 involves controlling an ultrasonic sensor array to acquire ultrasonic image data corresponding to at least one reflected ultrasonic wave received by at least a portion of the ultrasonic sensor array from a target object during an acquisition time window. According to some implementations, a control system (such as the control system 106) may be capable of controlling an ultrasonic sensor array such as one of those disclosed herein. In some examples, the acquisition time window may be selected to include an image of both fingerprint features and sub-epidermal features, if the target object is a finger. According to some examples, the acquisition time window may be selected to detect a common spoof that involves forming a fingerprint-like pattern on the outside of a sleeve, or the outside of a film, that may be worn on or slipped over an actual finger. According to some implementations, the acquisition time window may be in the range of 50 to 2000 nanoseconds, or in the range of approximately 50 to 2000 nanoseconds. However, in some implementations the acquisition time window may be in the range of 2000 to 10,000 nanoseconds, or in the range of approximately 2000 to 10,000 nanoseconds. In some examples the acquisition time window may be in the range of 10,000 to 20,000 nanoseconds, or in the range of approximately 10,000 to 20,000 nanoseconds.

Figure 5:
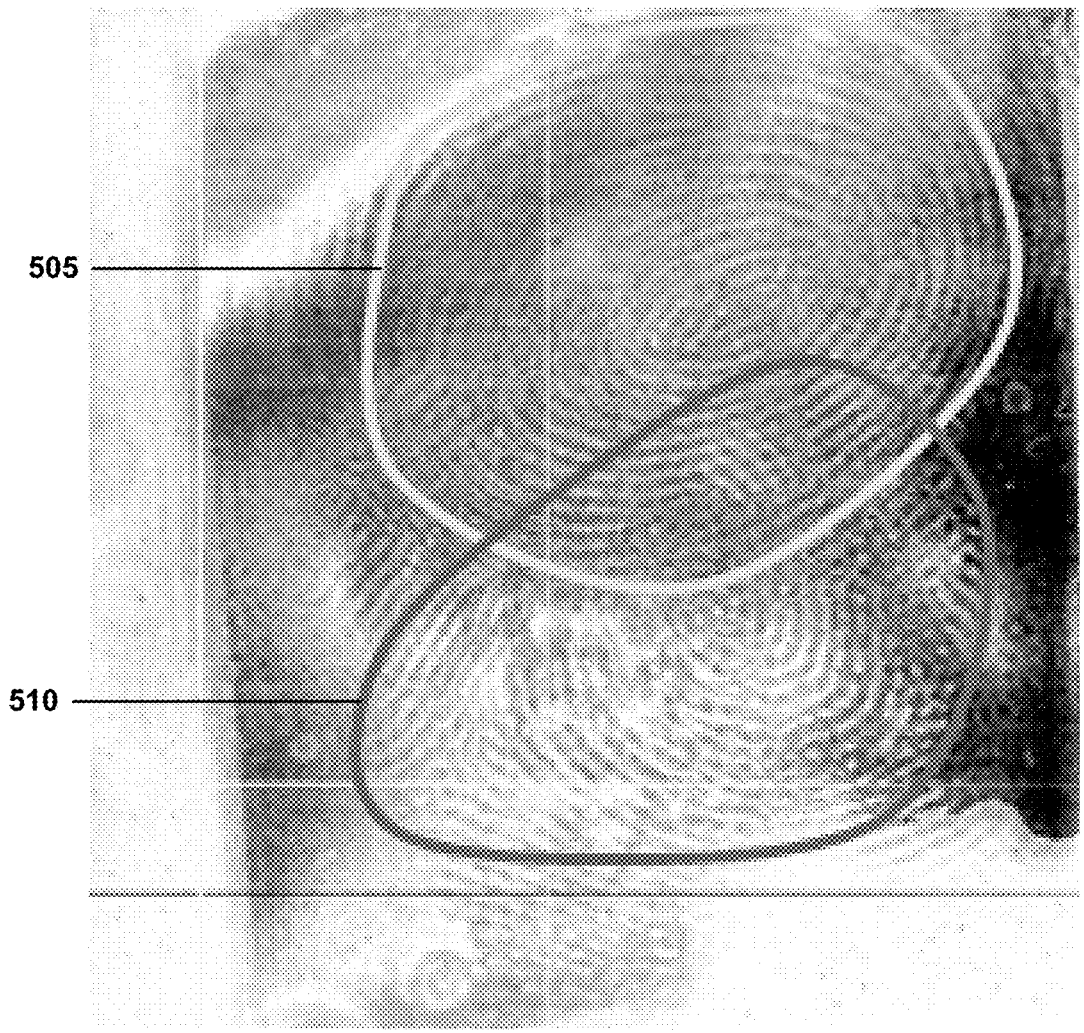
FIG. 5 shows an example of overlapping fingerprint images.

According to this example, block 310 involves extracting first fingerprint data from the ultrasonic image data. Here, block 315 involves determining whether the ultrasonic image data includes second fingerprint data that is different from the first fingerprint data. One example is shown in FIG. 5 and is described below. Visual inspection of FIG. 5 shows a prominent whorl and minutiae in the center of a finger of a live user (outline 505) along with a similarly prominent whorl and minutiae of a slipover spoof on the live user's finger (outline 510), which may be differentiated by a displacement in space even though only a single image was acquired using a relatively long acquisition time window. A control system may execute automated methods that may use minutiae and/or keypoints associated with the spoof and the underlying live user to attempt a match with one or more enrolled templates of a rightful user using fingerprint matching software. An automated fingerprint identification system (AFIS) or similar fingerprint analysis software may be used to identify both the live user and the spoof.

In some examples, block 315 may involve determining whether a depth difference between the depth of the first fingerprint data and the depth of the second fingerprint data corresponds to at least a threshold time difference, e.g., a time difference of more than 50 nanoseconds. If second fingerprint data are found at another depth, this is strong evidence of the type of spoof that is described above. For example, the second fingerprint data may correspond to the fingerprints of a hacker who has formed a spoof with an image of a fingerprint of a rightful user and has placed the spoof over the hacker's finger. In some examples, a control system will not continue an authentication process if second fingerprint data are found at another depth. In some such examples, a control system will not attempt to match the first or second fingerprint data with stored fingerprint data if second fingerprint data are found at another depth.

In some implementations, a spoof attempt may be flagged. In some such examples, a control system may generate a spoof-detected indication in response to a detected spoof attempt. In some implementations, a spoof-detected indication may initiate a routine to store images, minutiae and/or keypoints associated with the spoof and the hacker's finger. In some implementations, at least one of ultrasonic image data, first or second fingerprint data, fingerprint minutiae, fingerprint keypoints and/or fingerprint features may be stored when fingerprint features on the surface of a target object and different fingerprint features below the surface of the target object are detected. The stored images, image data, minutiae, keypoints, features and/or fingerprint data may be extracted at a later time in an attempt to identify the alleged hacker, particularly if one of the fingerprints (e.g. the spoof) corresponds to an authorized or otherwise enrolled user of a mobile device. A time stamp of the spoof attempt and, in some examples, other location and/or user information may also be stored for later use.

However, if it is determined that the ultrasonic image data does not include second fingerprint data that is different from the first fingerprint data, in this example an authentication process will be initiated based, at least in part, on the first fingerprint data. Some implementations may involve determining sub-epidermal features from the ultrasonic image data. In such examples, the authentication process may be based, at least in part, on the sub-epidermal features.

Some examples may involve making a liveness determination. Such a liveness determination may be useful for detecting spoofs in which a fingerprint image has been placed upon a finger-like object, which may be formed of rubber, silicon, etc. Some such liveness determinations may involve obtaining first sub-epidermal features from first ultrasonic image data at a first time and obtaining second sub-epidermal features from second ultrasonic image data at a second time. Some examples may involve making a liveness determination based on a change between the first sub-epidermal features and the second sub-epidermal features. This type of temporal change may, for example, correspond with the flow of blood within a finger.

Figure 3B:
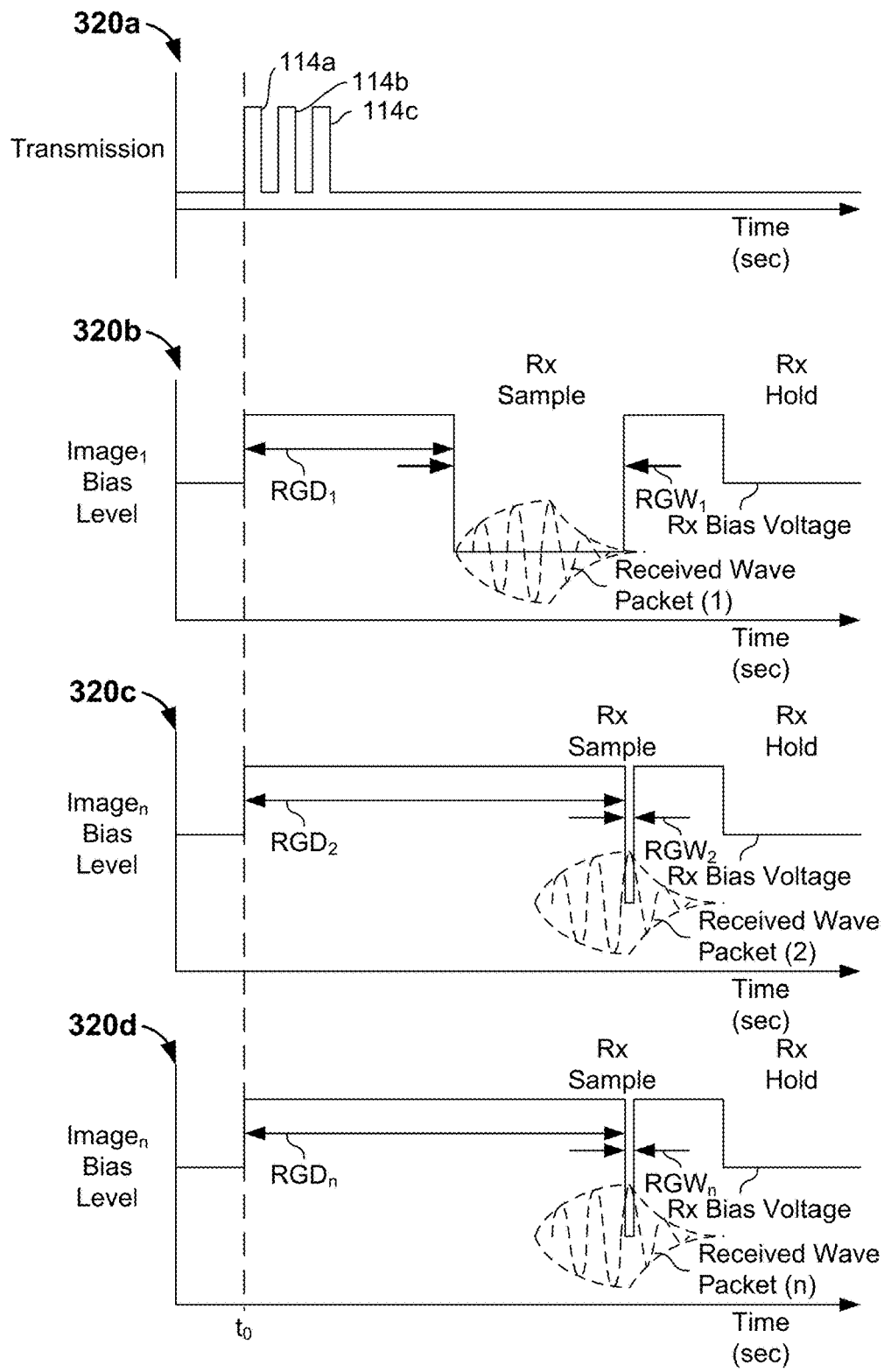
FIG. 3B shows some alternative examples of acquisition time delays and acquisition time windows.

FIG. 3B shows some alternative examples of acquisition time delays and acquisition time windows. The acquisition time delays and acquisition time windows shown in FIG. 3B may, for example, be appropriate for the methods described above with reference to FIG. 1C and/or FIG. 3A.

Graph 320a shows transmitted signals 114a, 114b and 114c, the first of which is initiated at a time $t_0$. In this example, the transmitted signals 114a, 114b and 114c are pulses of ultrasound. In alternative examples, a single pulse of ultrasound may be transmitted. In some implementations, the transmitted signals may include waveforms of other shapes, such as sinusoidal, triangular, rectangular, square, single-sided, double-sided, alternating, single-frequency, multi-frequency, chirped, low duty cycle, high duty cycle, modulated, double-modulated, or a combination of one or more such waveforms.

Graph 320b shows examples of a first acquisition time delay $RGD_1$ and a first acquisition time window $RGW_1$. The received wave packet (1) represents reflected waves that are received by an ultrasonic sensor array and sampled during the first acquisition time window $RGW_1$, after the first acquisition time delay $RGD_1$. In some examples, the first acquisition time delay may correspond to a time required for a transmitted ultrasonic wave to be reflected from a surface of a platen and received by at least a portion of the ultrasonic sensor array.

The first acquisition time window may, in some examples, correspond with the acquisition time window described above with reference to block 305 of FIG. 3A. According to some examples, the first acquisition time window may be in the range of 50 to 2000 nanoseconds, or in the range of approximately 50 to 2000 nanoseconds. However, in some implementations the first acquisition time window may be in the range of 2000 to 10,000 nanoseconds, or in the range of approximately 2000 to 10,000 nanoseconds. In some examples the first acquisition time window may be in the range of 10,000 to 20,000 nanoseconds, or in the range of approximately 10,000 to 20,000 nanoseconds. In some examples, the first acquisition time delay and the first acquisition time window may correspond to a fingerprint feature of the target object and to one or more sub-epidermal features of the target object.

Graph 320c shows examples of a second acquisition time delay $RGD_2$ and a second acquisition time window $RGW_2$. The received wave packet (2) represents reflected waves that are received by an ultrasonic sensor array and sampled during the second acquisition time window $RGW_2$, after the second acquisition time delay $RGD_2$. Graph 320d shows examples of an $n^{th}$ acquisition time delay $RGD_n$ and an $n^{th}$ acquisition time window $RGW_n$, wherein n is an integer greater than 2. In some examples, n may be 3, 4, 5, etc. The received wave packet (n) represents reflected waves that are received by an ultrasonic sensor array and sampled during the $n^{th}$ acquisition time window $RGW_n$, after the $n^{th}$ acquisition time delay $RGD_n$.

In this example, the second acquisition time delay equals the $n^{th}$ acquisition time delay and the second acquisition time window equals the $n^{th}$ acquisition time window. According to some examples, the graphs 320c and 320d may correspond to a process of obtaining ultrasonic data for a liveness determination from the same depth inside a target object at two or more different times. Temporal-based feature differences between the ultrasonic data may be evidence of liveness. In other implementations, the second and $n^{th}$ acquisition time delays and/or the second and $n^{th}$ acquisition time windows may differ from one another.

In some implementations, the second and $n^{th}$ acquisition time windows may be in the range of about 5 to 50 nanoseconds, or in the range of approximately 5 to 50 nanoseconds. However, in some implementations the second and $n^{th}$ acquisition time windows may be in the range of 50 to 2000 nanoseconds, or in the range of approximately 50 to 2000 nanoseconds. According to some examples, the second and $n^{th}$ acquisition time delays and time windows may correspond to a sub-epidermal feature of the target object, such as a blood vessel feature.

In this example, the acquisition time delays are both measured from the time $t_0$. However, in other implementations, the acquisition time delays may be measured from a different initial time.

FIG. 4 shows an example of an image of a fingerprint superimposed on multiple sub-epidermal features. In FIG. 4, an acquisition time delay and a relatively long acquisition time window have been selected in order to obtain a composite, overlapping and self-referencing image of lobules (the grayish blobs, such as the blob 405) and other sub-surface features automatically overlaid on a fingerprint image. Note that some of the grayish blobs in FIG. 4 are readily referenced with respect to various fingerprint minutiae of the finger such as ridge endings or bifurcations. In some such implementations, an authentication process may be based upon data extracted from both the fingerprint image and the images of sub-epidermal features or from data extracted from a single image that contains both the fingerprint and the sub-epidermal features. For example, attribute information based on ultrasonic images of sub-epidermal features may be referenced to attribute information based on ultrasonic fingerprint images. According to some such implementations, biometric template data corresponding to sub-epidermal features may be referenced to biometric template data corresponding to fingerprint features, such as the locations, orientations and/or types of fingerprint minutiae. In some implementations, a composite image including fingerprint and sub-epidermal features may be compared to an enrolled fingerprint template containing fingerprint and sub-epidermal template information or only fingerprint-related template information for validation and authentication.

As noted above, some implementations may involve selecting an acquisition time delay and an acquisition time window in order to determine whether a sleeve or a film having a fingerprint formed on it has been placed over or on a hacker's finger in a spoofing attempt. If so, two sets of overlapping fingerprint images may be obtained, one of the fake fingerprint and the other from the hacker's finger.

FIG. 5 shows an example of overlapping fingerprint images. In order to produce the image shown in FIG. 5, a human finger (the fingerprint of which is indicated within the outline 505) was positioned behind a polydimethylsiloxane (PDMS) spoof finger with a thickness of about 0.5 millimeter having replicated fingerprints (indicated within the outline 510) that were simultaneously imaged with a 1"×1" ultrasonic sensor array using a relatively large RGW. The spoof and real fingerprints may, for example, correspond to the first and second fingerprint data that are described above with reference to FIG. 3A. In the example shown in FIG. 5, the spoof and real fingerprints were intentionally offset for clarity. A control system may run fingerprint analysis software to authenticate a user based on the spoof and real fingerprints. In some implementations, the fingerprint analysis software may adequately recognize the fingerprint of an authorized user despite the complexity of additional minutiae and fingerprint features. If the number of fingerprint features exceeds that of an enrolled fingerprint, a spoof attempt may be ascertained and additional images at different depths in the target object may be acquired to validate a spoof attempt. In some implementations, a detected spoof attempt may initiate a process to store fingerprint images, minutiae and/or keypoints associated with the spoof and the hacker's finger for the composite image and/or the images at different depths. The stored images, minutiae and/or keypoints may be used at a later time to identify an alleged hacker. A time stamp of the image acquisition may be stored with the fingerprint images, minutiae and/or keypoints.

Some implementations may involve an authentication process that is based on both a liveness determination and attribute information obtained from ultrasonic image data corresponding to sub-epidermal features. Some such implementations may involve obtaining image data corresponding to sub-epidermal features, determining biometric template data corresponding to the obtained image data and comparing the determined biometric template data with stored biometric template data of a rightful user.

The liveness determination may be made in a variety of ways, depending on the particular implementation. In addition to providing information regarding sub-epidermal features of a target object, such as structures within a finger, in some implementations temporal changes in the time difference between reflections of simple A-scans, obtained at two or more different times, may be used to detect liveness.

Figure 6A:
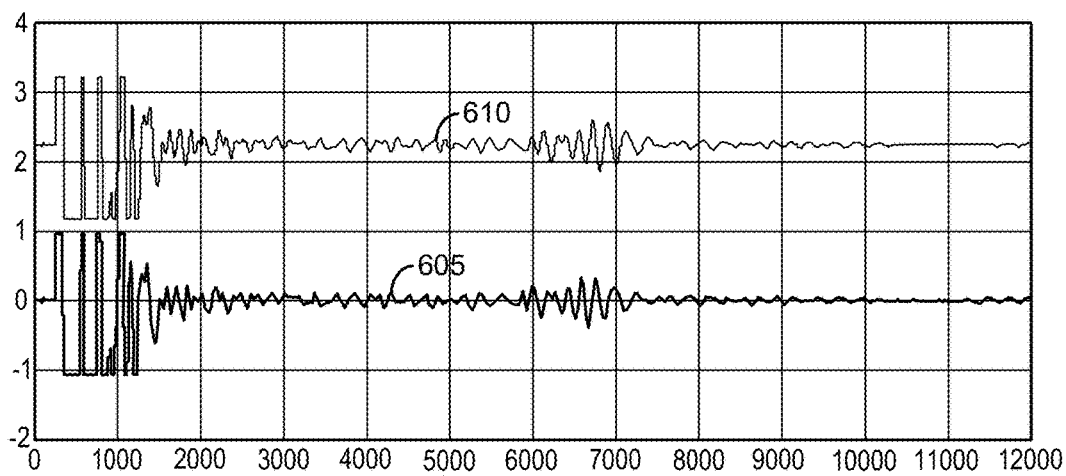
FIGS. 6A-6C are graphs that show an example of a time difference between reflections of two A-scans.
Figure 6B:
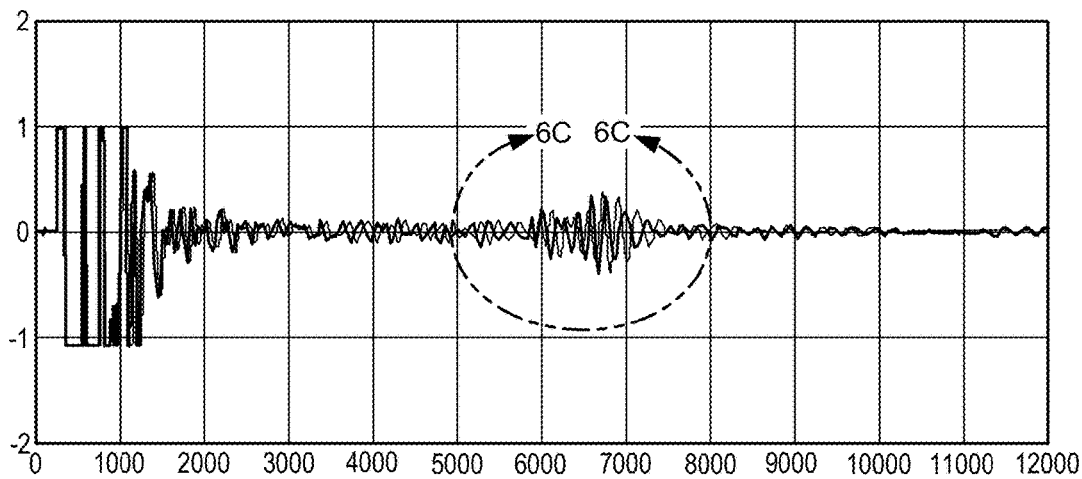
Figure 6C:
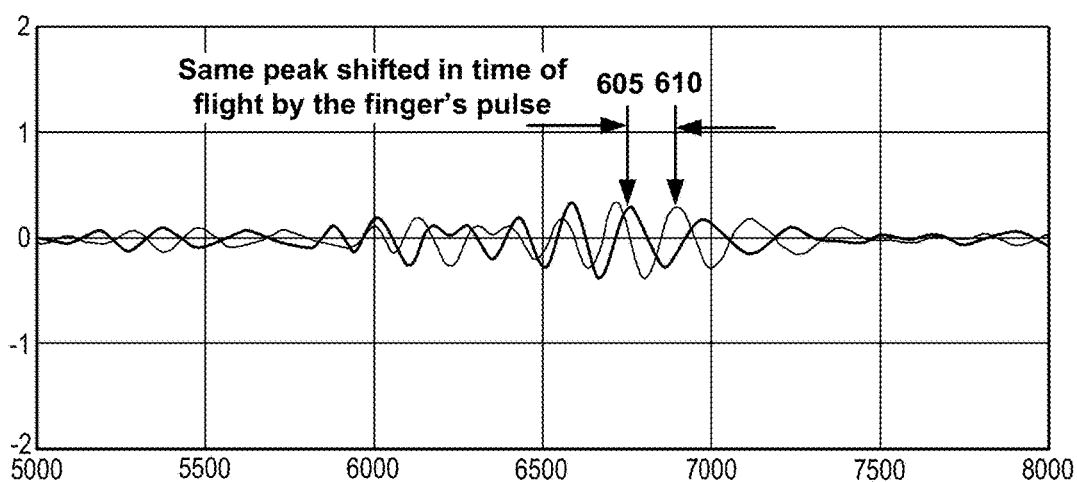

FIGS. 6A-6C are graphs that show an example of a time difference between reflections of two A-scans. FIG. 6A shows an A-scan plot 605, which was obtained at a first time, and an A-scan plot 610 that was obtained at a second time. FIG. 6B shows the A-scan plots 605 and 610 superimposed along the same vertical axis. FIG. 6C is an enlarged view of the corresponding region within dashed lines, labeled 6C, in FIG. 6B. In this example, time differences between the A-scan plots 605 and 610 are caused by tissue expansion and contraction as blood pulses through the finger's vascular system. This expansion and contraction due to pulse activity can be seen in the A-scan plot as a small shift in the time of flight of the plotted return echoes. Similar temporal variations may be determined from associated B-scans, C-scans or volumetric scans (e.g. combinations of B-scans and/or C-scans).

Depth imaging and processing of the acquired images can take inordinate resources of power and processing capability in mobile devices. In some implementations, depth images of selected pores, follicles or other epidermal or sub-epidermal features may be acquired, analyzed and compared to enrollment templates to detect a spoof attempt, minimizing processing time and power while ascertaining liveness and determining whether the user is to be authenticated or otherwise validated.

FIGS. 7-11B are flow diagrams that provide additional examples of biometric system operations. The blocks of FIGS. 7-11B (and those of other flow diagrams provided herein) may, for example, be performed by the apparatus 101 of FIG. 1B or by a similar apparatus. As with other methods disclosed herein, the methods outlined in FIGS. 7-11B may include more or fewer blocks than indicated. Moreover, the blocks of the methods disclosed herein are not necessarily performed in the order indicated.

Figure 7:
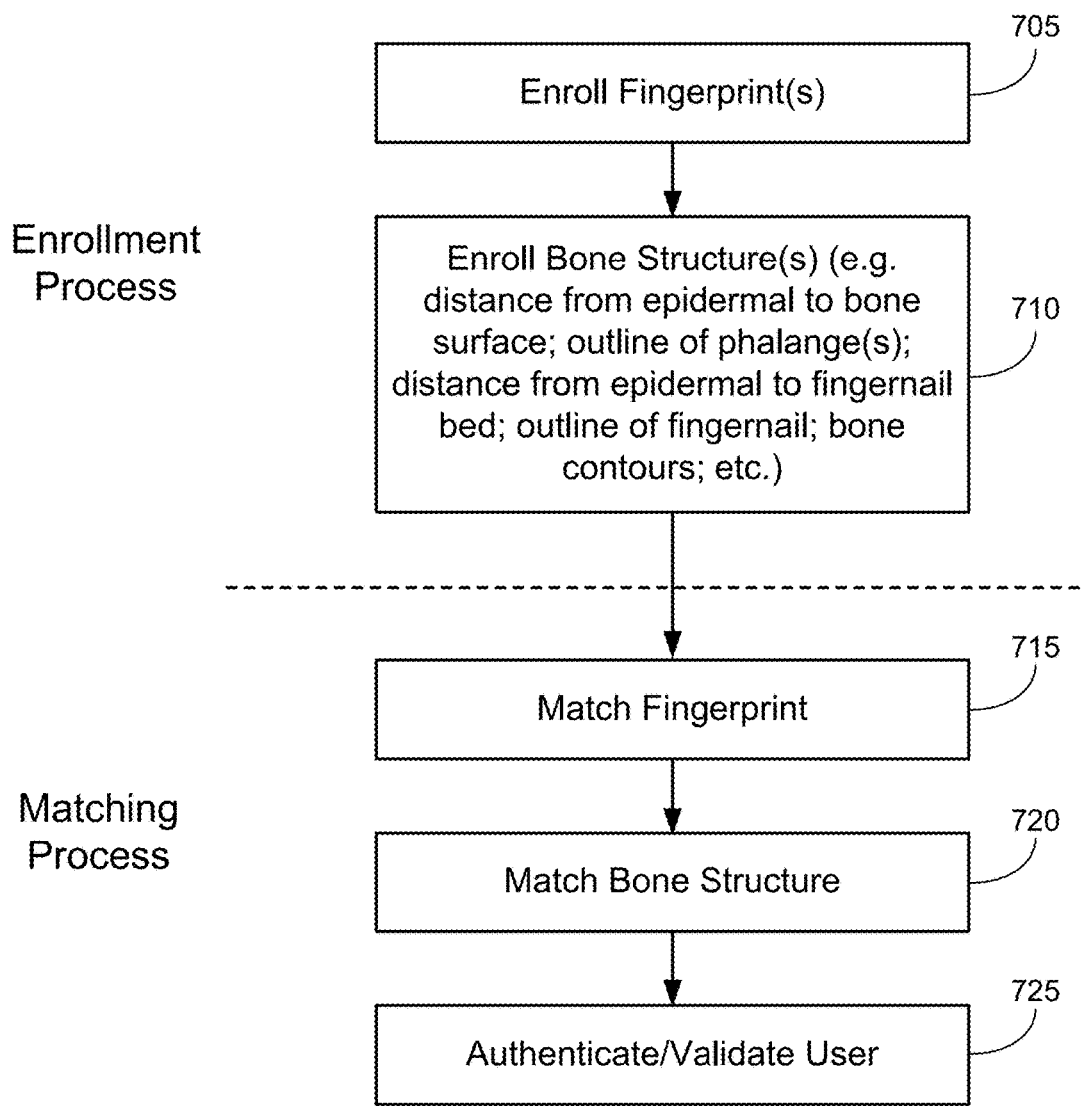
FIG. 7 shows examples of enrollment and matching processes utilizing fingerprint and bone structures.

FIG. 7 shows an example of enrollment and matching processes utilizing fingerprint and bone structures. During an enrollment process, one or more fingers of a rightful user may be enrolled in block 705. The enrollment process may generate an enrollment template containing information about the fingerprint of the rightful user, such as fingerprint minutiae or keypoints. The enrollment template may include additional enrollment information about the finger, such as bone structures, which are obtained in block 710 in this example. Information about the bone structures may include, for example, distances from the epidermal layer to the bone surface, an outline of the phalangeal bones, distances from the epidermal layer to the fingernail bed, an outline of the fingernail bed, bone contours, etc. A matching process may attempt to match fingerprint information from a potential user (block 715) along with information about the bone structure and other sub-epidermal features (block 720) to one or more enrollment templates. If the fingerprint and sub-epidermal features match with an enrollment template, the potential user may be authenticated or may be otherwise validated (block 725.

Figures 8A, 8B:
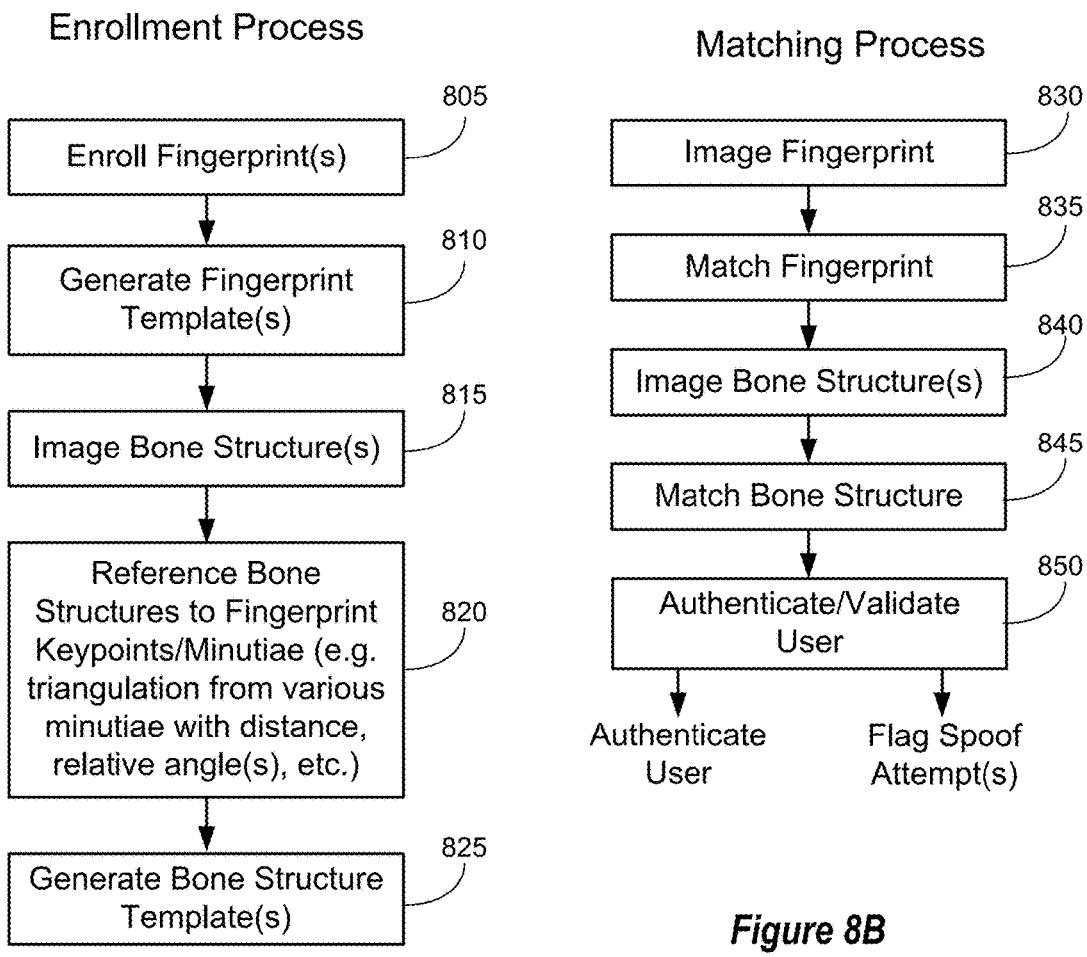
FIGS. 8A and 8B show examples of enrollment and matching processes utilizing fingerprint and bone structures.

FIGS. 8A and 8B show examples of enrollment and matching processes utilizing fingerprint and bone structures. FIG. 8A illustrates steps of an enrollment process where one or more fingerprints are enrolled in block 805. One or more enrollment templates may be generated from the fingerprint information during enrollment, in block 810. Additionally, bone structures within the finger may be imaged in block 815. In some implementations, the bone structure may be referenced, in block 820, to selected keypoints or minutiae of the fingerprint. For example, triangulation may be used from various selected minutiae to determine distance, offset and relative angles with respect to the selected reference point. An enrollment template with the bone structure information may be generated and stored in block 825. In some implementations, the bone structure information may be stored in the same enrollment template as the fingerprint information.

During a matching process as illustrated in FIG. 8B, a fingerprint of a potential user is imaged in block 830, and an authentication template generated from the fingerprint information may be matched to one or more enrollment templates in block 835. If a match is determined, various bone structures or other sub-epidermal features may be imaged in block 840 and matched in block 845 to an associated enrollment template. If both the fingerprint features and sub-epidermal features are matched, then the potential user may be authenticated in block 850. In some implementations, if no bone structures or recognizable sub-epidermal features are detected, a spoof-detected indication may be generated in block 850.

Figure 9:
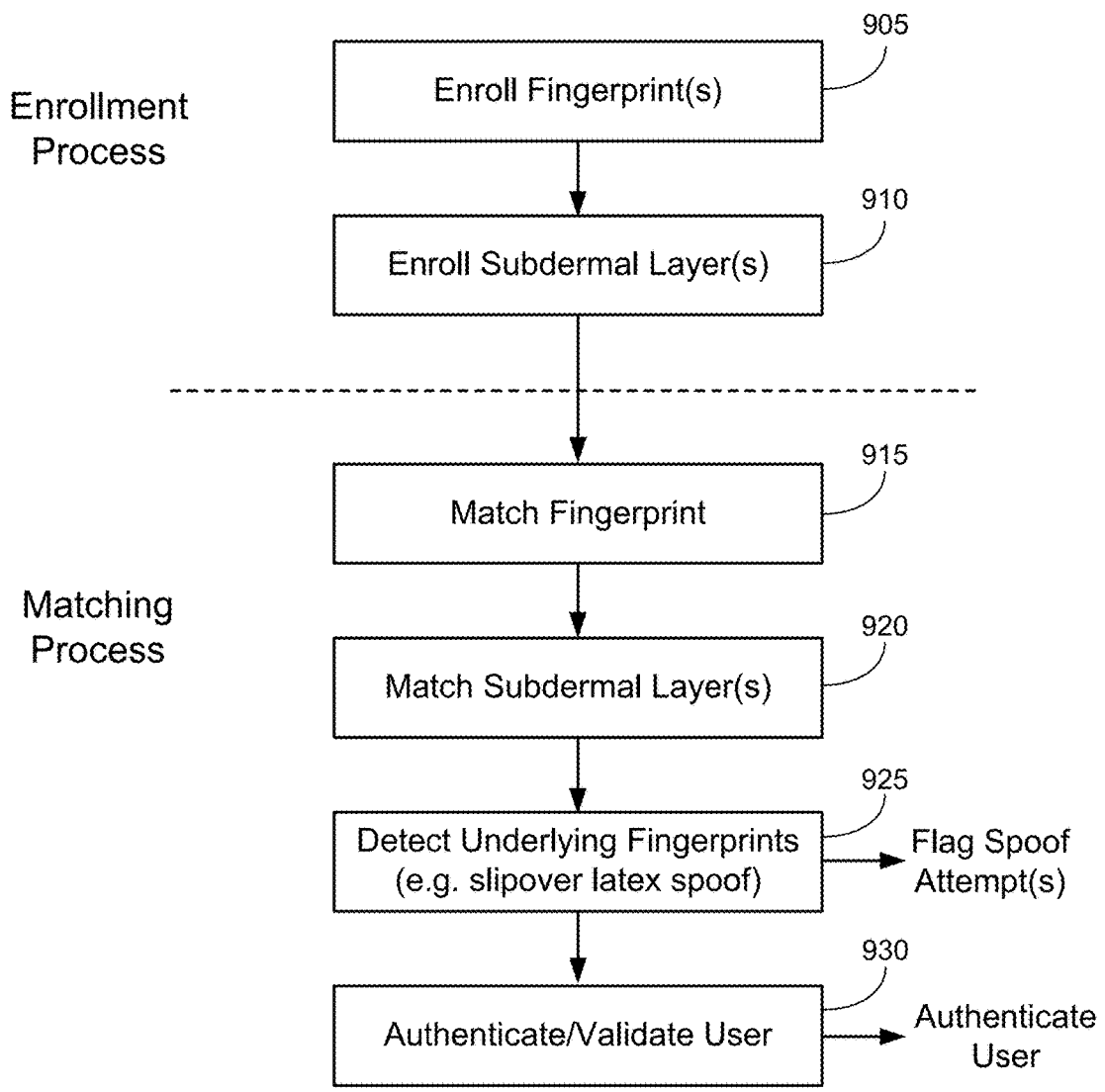
FIG. 9 show examples of enrollment and matching processes for the detection of slipover fingerprint spoofs such as a sleeve spoof.

FIG. 9 shows an example of enrollment and matching processes for the detection of slipover fingerprint spoofs such as a sleeve spoof. During an enrollment process, one or more enrollment templates may be generated for the fingerprint of a rightful user in block 905. In block 910, one or more enrollment templates may be generated for sub-epidermal layers of a rightful user. During the matching process of blocks 915 and 920, attempts to match the fingerprint and sub-epidermal layers of a potential user may be made. In some implementations, a spoof attempt may be flagged in block 925 when an underlying fingerprint is detected, such as may occur when an slipover spoof of an enrolled user is placed over a hacker's finger. For example, a spoof attempt may be flagged by setting a spoof-detected indication such as a spoof detection output signal or a spoof detection flag to an affirmative value. If a spoof is not detected, then the potential user may be authenticated or otherwise validated in block 930.

Figures 10A, 10B:
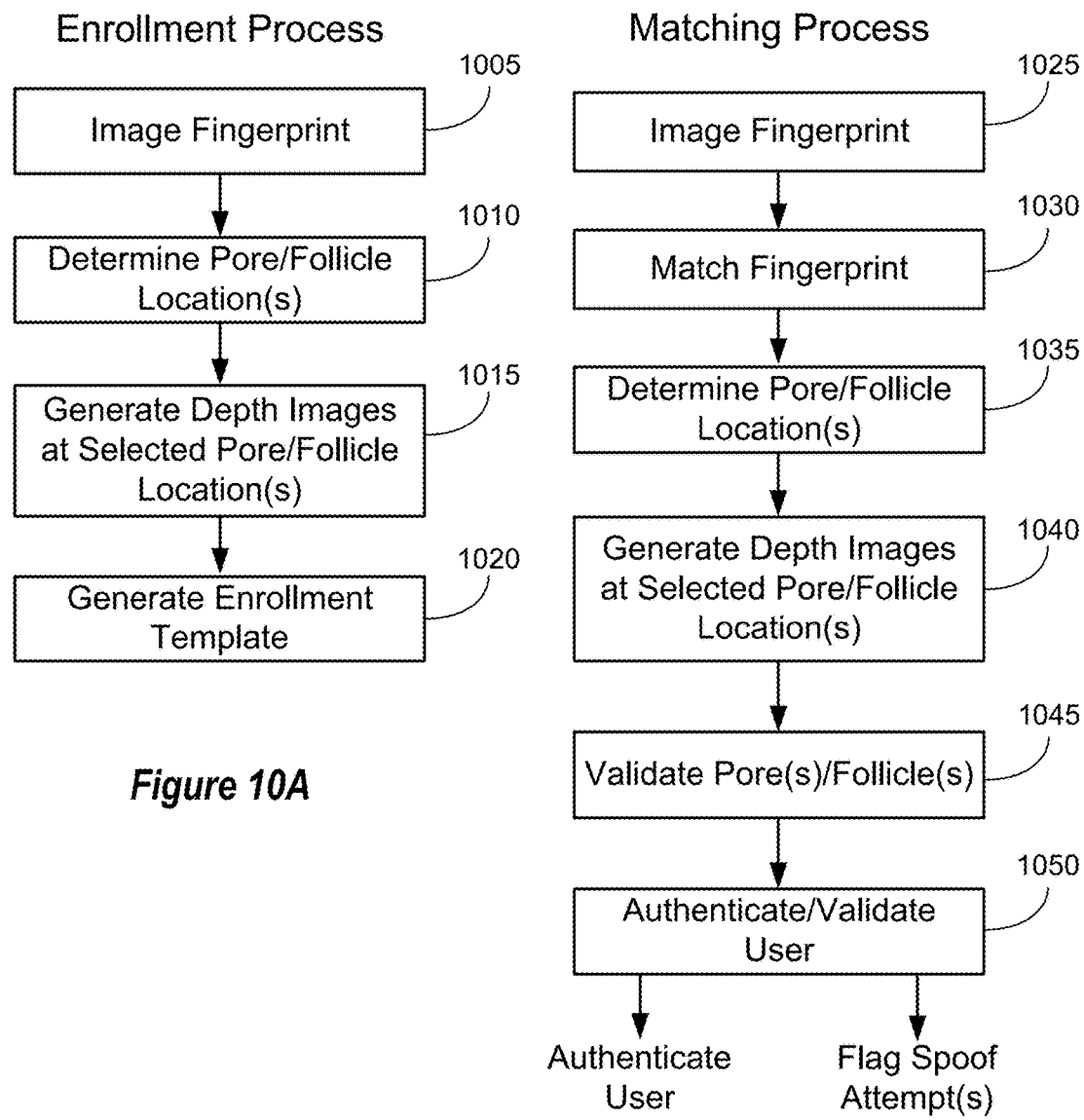
FIGS. 10A and 10B show examples of enrollment and matching processes with fingerprint and pore/follicle locations.

FIGS. 10A and 10B show examples of enrollment and matching processes with fingerprint and pore/follicle locations. In the example of FIG. 10A, a fingerprint image is obtained during block 1005 of an enrollment process. Fingerprint image data, such as fingerprint template data, may be determined from the fingerprint image in block 1010 and stored in some implementations. Pore and/or follicle feature locations, or other feature locations (such as sub-epidermal feature locations) may then be determined. Depth images of selected pore and/or follicle features, or other features (such as sub-epidermal features) may then be generated in block 1015. An enrollment template corresponding to the pore and/or follicle images with or without fingerprint minutiae information may then be generated in block 1020 and stored for future reference.

In the example of FIG. 10B, a new fingerprint image is obtained during block 1025 of a subsequent authentication process. It may then be determined, in block 1030, whether fingerprint data corresponding to the new fingerprint image matches the stored fingerprint data (e.g., fingerprint template data). Pore and/or follicle feature locations, or other feature locations (such as sub-epidermal feature locations) may then be determined in block 1035. Depth images of selected pore and/or follicle features, or other features (such as sub-epidermal features) may then be generated in block 1040. An authentication template for the selected pore and/or follicle images may be determined. A process of validating the authentication template for the selected pore and/or follicle images (block 1045) may involve comparing the authentication template with the enrollment template. If both the fingerprint template data and the template for the selected pore and/or follicle images match the data stored during the enrollment process, a user may be authenticated in block 1050. In some implementations, if an authentication template of a fingerprint fails to match with enrolled templates of a fingerprint, the steps related to sub-surface imaging may be omitted to reduce processing time and power consumption.

Figures 11A, 11B:
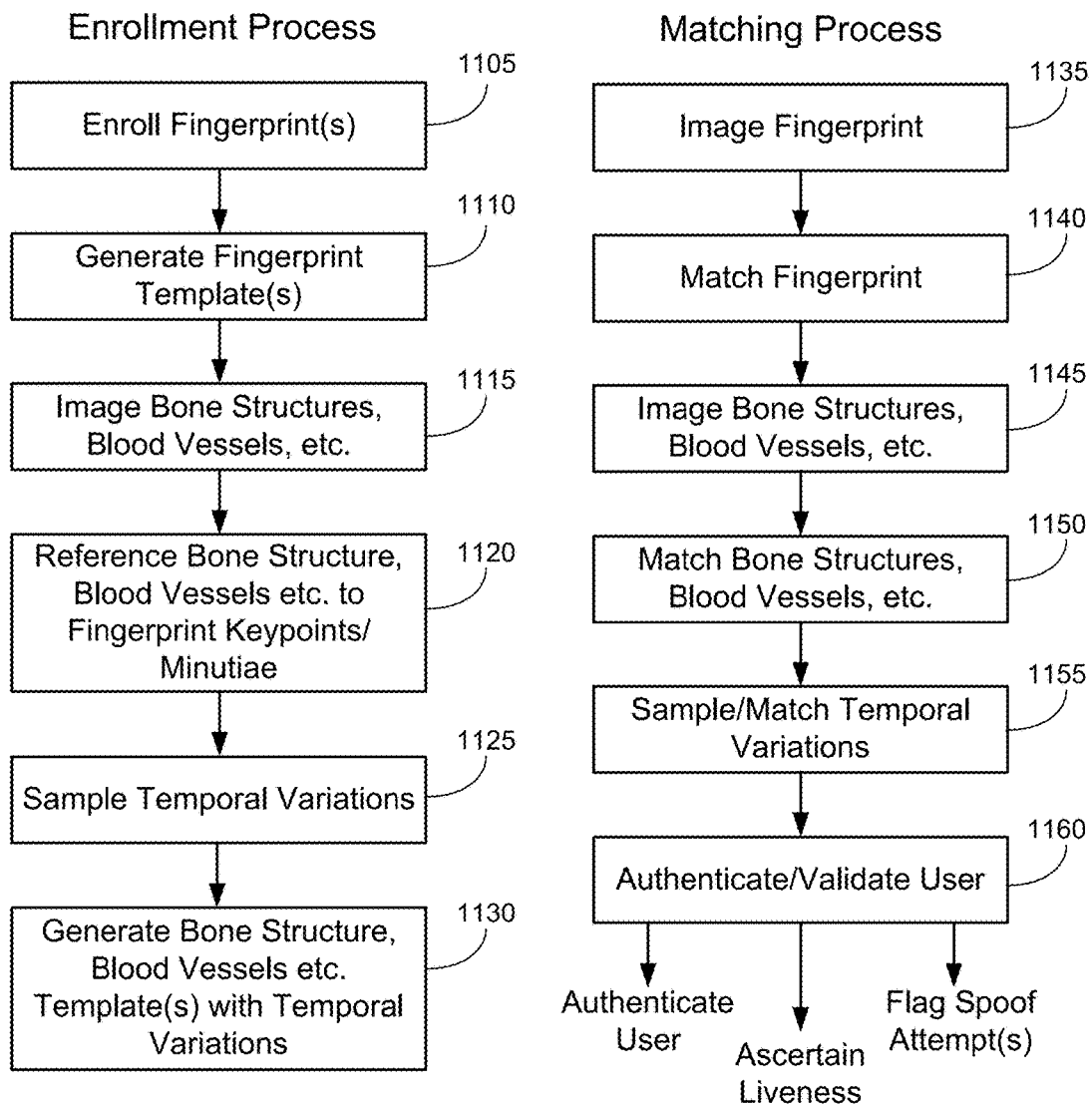
FIGS. 11A and 11B show examples of enrollment and matching processes with depth profiling and temporal changes.

FIGS. 11A and 11B show examples of enrollment and matching processes with depth profiling and temporal changes. During an enrollment process shown in FIG. 11A, one or more fingerprints of a rightful user may be enrolled in block 1105. One or more fingerprint templates may be generated in block 1110. Bone structure, blood vessels and other sub-epidermal structures may be imaged in block 1115, e.g., using selected range-gate delays and range-gate windows. The bone structures, blood vessels and other sub-epidermal features may be referenced to fingerprint keypoints or minutiae in block 1120. During enrollment, various images may be acquired and temporal variations of the bone structures, blood vessels or other sub-epidermal features may be sampled in block 1125, such as variations in the outline of a bone or fat lobule with respect to one or more minutia or other reference point. A template with the bone structure, blood vessels or other sub-epidermal features along with their characteristic temporal variations may be generated in block 1130 and stored as a separate enrollment template or added to the fingerprint enrollment template.

During a matching process shown in FIG. 11B, a fingerprint of a potential user may be imaged in block 1135 and matched to one or more stored enrollment templates in block 1140. If a match is made, bone structures, blood vessels or other sub-epidermal features may be imaged in block 1145 and matched to a stored enrollment template in block 1150. If the match is successful, temporal variations in the bone structures, blood vessels or other sub-epidermal features with respect to one or more fingerprint minutia or reference points may be sampled in block 1155 and compared to stored temporal information in the enrollment template. The potential user may be authenticated in block 1160 based on the matching of the fingerprint, sub-epidermal features and/or temporal variations. In some implementations, liveness may be ascertained from the temporal variations in block 1160. A liveness indicator may be generated based on the temporal-based feature differences between two or more sub-epidermal images in block 1160. A spoof-detected indication may be generated in block 1160 based on differences between the fingerprint features on the surface of the target object and the fingerprint features below the surface of the target object and the lack or existence of temporal variations.

During a conventional process of obtaining a fingerprint image, only a 2-D image is normally acquired. Such 2-D fingerprint images lack some information related to the actual geometry of the fingerprint, such as ridge-valley depth. Some forms of a spoofed fingerprint may lack such 3-D features. Therefore, evaluating such 3-D features can both increase the accuracy of a fingerprint matching process and be at least one factor in a spoof detection process.

Accordingly, some implementations involve obtaining a 3-D image of at least a portion of a target object. In some examples, the 3-D image may be obtained from a relatively shallow depth and may be a 3-D image of a fingerprint.

Figure 12:
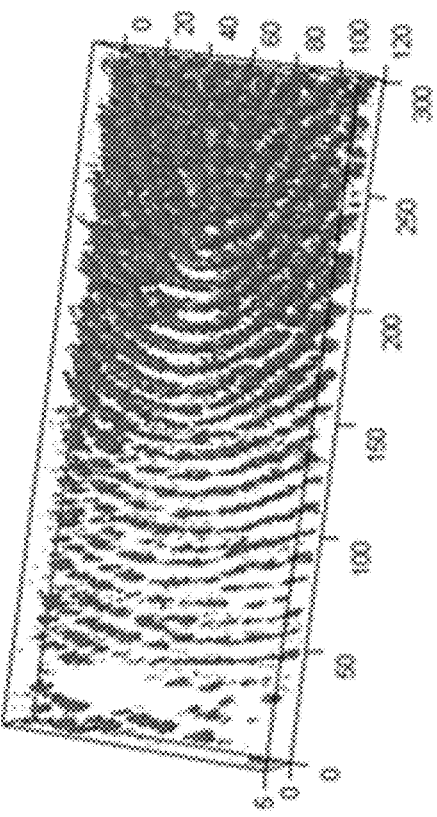
FIG. 12 shows an example of a 3-D image of a fingerprint.

FIG. 12 shows an example of a 3-D image of a fingerprint. The dimensions shown in FIG. 12 are merely examples. Some implementations may involve obtaining ultrasonic image data at one or more depths suitable for obtaining one or more 3-D images of sub-epidermal features. As noted above, the depths may correspond with selected acquisition time delays. In some implementations, 3-D or volumetric images of a finger may be constructed from a larger number of A-scan images, B-scan images or C-scan images.

In some instances, a control system may be capable of acquiring first through $N^{th}$ ultrasonic image data during first through $N^{th}$ acquisition time windows after first through $N^{th}$ acquisition time delays. Each of the first through $N^{th}$ acquisition time delays may correspond to a first through an $N^{th}$ depth inside the target object. For example, a volumetric image of a finger or a finger portion may be generated from multiple acquisitions of image data at various depths into the finger or along particular finger features such as hair follicles or sweat pores.

Some implementations may involve selecting one or more acquisition time delays and/or acquisition time windows (also referred to as a range-gate window or RGW) as part of an authentication or a spoof detection process. For example, if a sleeve having a fingerprint formed on it has been placed on or over a hacker's finger, there should be a relatively homogeneous sleeve layer between the fake fingerprint and the hacker's finger that does not include sub-epidermal features that are characteristic of a finger. Therefore, in order to evaluate whether a sleeve having a fingerprint formed on it has been placed over a hacker's finger in a spoofing attempt, one or more acquisition time delays with a relatively short RGW may be selected to determine whether there is a layer beneath a fingerprint layer that does not appear to include features that are characteristic of a finger. Some such implementations may involve selecting one or more acquisition time delays and acquisition time windows suitable for determining whether there is a second fingerprint beneath a sleeve/non-finger layer, such as a fingerprint of a rightful user positioned over a fingerprint of an imposter. Some implementations may involve selecting one or more finger features such as a sweat pore and imaging the region of the sweat pore at various depths interior to the finger surface to verify that the feature is continuous and characteristic of the rightful user's finger rather than a spoof.

Alternatively, or additionally, some implementations may involve selecting one or more acquisition time windows as part of an authentication or a spoof detection process. In some such examples, an acquisition time delay and a relatively long acquisition time window may be selected in order to obtain image data that includes a fingerprint image superimposed on an image of one or more sub-epidermal features.

In some implementations, a receiver bias control signal may be applied to a receiver bias electrode that is coupled to a piezoelectric receiver layer associated with an ultrasonic sensor array. The ultrasonic sensor array may include an array of sensor pixel circuits configured on a silicon, glass or plastic substrate. In some implementations, the sensor pixel circuits may comprise a collection of silicon or thin-film transistors, capacitors and a diode for rectifying and capturing signal information when the piezoelectric receiver layer receives an ultrasonic wave. One or more ultrasonic waves may be launched from an ultrasonic transmitter and reflected from a surface of a platen coupled to the ultrasonic sensor array. A finger or other target object placed on the surface of the platen may be imaged due to acoustic impedance mismatches between the platen and portions of the finger (e.g., ridges and valleys). The amplitude of the reflected waves depends in part on the degree of acoustic impedance mismatch at the platen surface. Selection of an appropriate RGD and a relatively narrow RGW allows images of the fingerprint ridges and valleys at the surface of the platen to be acquired by the ultrasonic sensor array.

Figure 13:
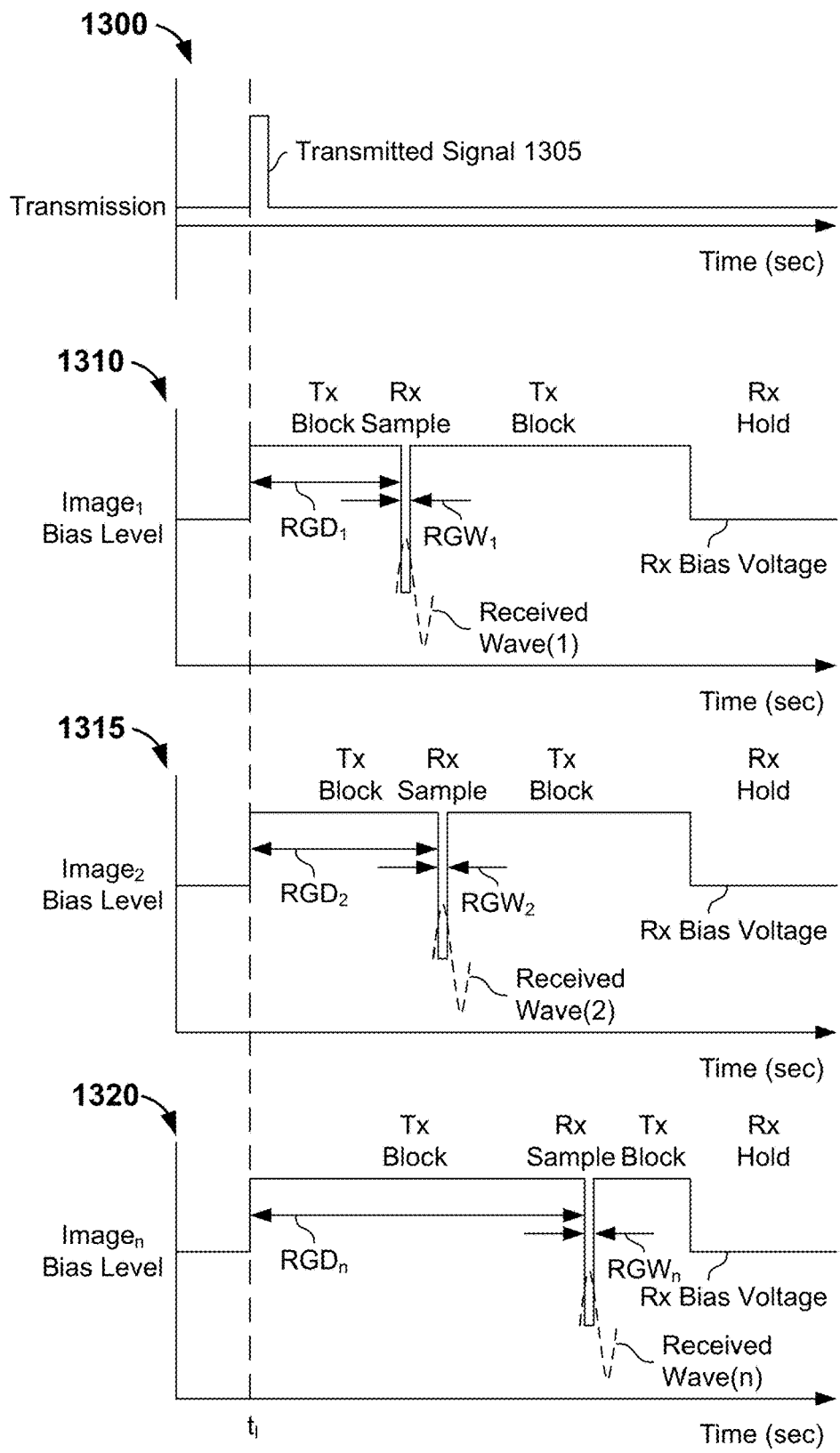
FIG. 13 shows examples of multiple acquisition time delays being selected to receive acoustic waves reflected from different depths.

FIG. 13 shows examples of multiple acquisition time delays being selected to receive acoustic waves reflected from different depths. In these examples, each of the acquisition time delays (which are labeled range-gate delays or RGDs in FIG. 13) is measured from the beginning time $t_1$ of the transmitted signal 1305 shown in graph 1300. The graph 1310 depicts reflected acoustic waves (received wave (1) is one example) that may be received by an ultrasonic sensor array at an acquisition time delay $RGD_1$ and sampled during an acquisition time window of $RGW_1$. Such acoustic waves will generally be reflected from a relatively shallower portion of a target object proximate, or positioned upon, a platen of the biometric system.

Graph 1315 depicts reflected acoustic waves (received wave (2) is one example) that are received by at least a portion of the ultrasonic sensor array at an acquisition time delay $RGD_2$ (with $RGD_2 > RGD_1$) and sampled during an acquisition time window of $RGW_2$. Such acoustic waves will generally be reflected from a relatively deeper portion of the target object. Graph 1320 depicts reflected acoustic waves (received wave (n) is one example) that are received at an acquisition time delay $RGD_n$ (with $RGD_n > RGD_2 > RGD_1$) and sampled during an acquisition time window of $RGW_n$. Such acoustic waves will generally be reflected from a still deeper portion of the target object.

Range-gate delays are typically integer multiples of a clock period. A clock frequency of 128 MHz, for example, has a clock period of 7.8125 nanoseconds, and RGDs may range from under 10 nanoseconds to over 20,000 nanoseconds.

Similarly, the range-gate windows may also be integer multiples of the clock period, but are often much shorter than the RGD (e.g. less than about 50 nanoseconds) to capture returning signals while retaining good axial resolution. In some implementations, the acquisition time window (RGW) may be between about 10 nanoseconds to about 200 nanoseconds. In some examples, the RGW may be less than 10 nanoseconds, e.g., 5 nanoseconds, 6 nanoseconds, 7 nanoseconds or 8 nanoseconds. Such implementations may be advantageous for acquiring ultrasonic data for a 3D image, e.g., for a 3D fingerprint image. However, in some examples the RGW may be more than 200 nanoseconds.

Extending the duration of the range-gate width while keeping the RGD constant allows the sensor pixel circuits to capture the peak value of the reflected ultrasonic waves corresponding to the fingerprint ridges and valleys and to sub-epidermal features that may be captured during the time that the RGW is active. Increasing the RGD allows imaging of sub-epidermal features deeper into the finger.

Note that while various image bias levels (e.g. Tx block, Rx sample and Rx hold that may be applied to an Rx bias electrode) may be in the single or low double-digit volt range, the return signals may have voltages in the tens or hundreds of millivolts. In some implementations, the receiver bias control signal having two or more levels representing the selected RGD and RGW may be applied to the receiver bias electrode of the ultrasonic sensor array. In some implementations, a diode bias control signal applied to the sensor pixel circuits within the ultrasonic sensor array may contain two or more levels representing the selected RGD and RGW. In some implementations, a portion of the sensor pixel circuits, such as a block, line or sub-array of pixels, may be used to acquire one or more images in a sub-surface region of the target object at the desired depth and position to increase the frame rate and reduce the image processing requirements.

Figure 14:
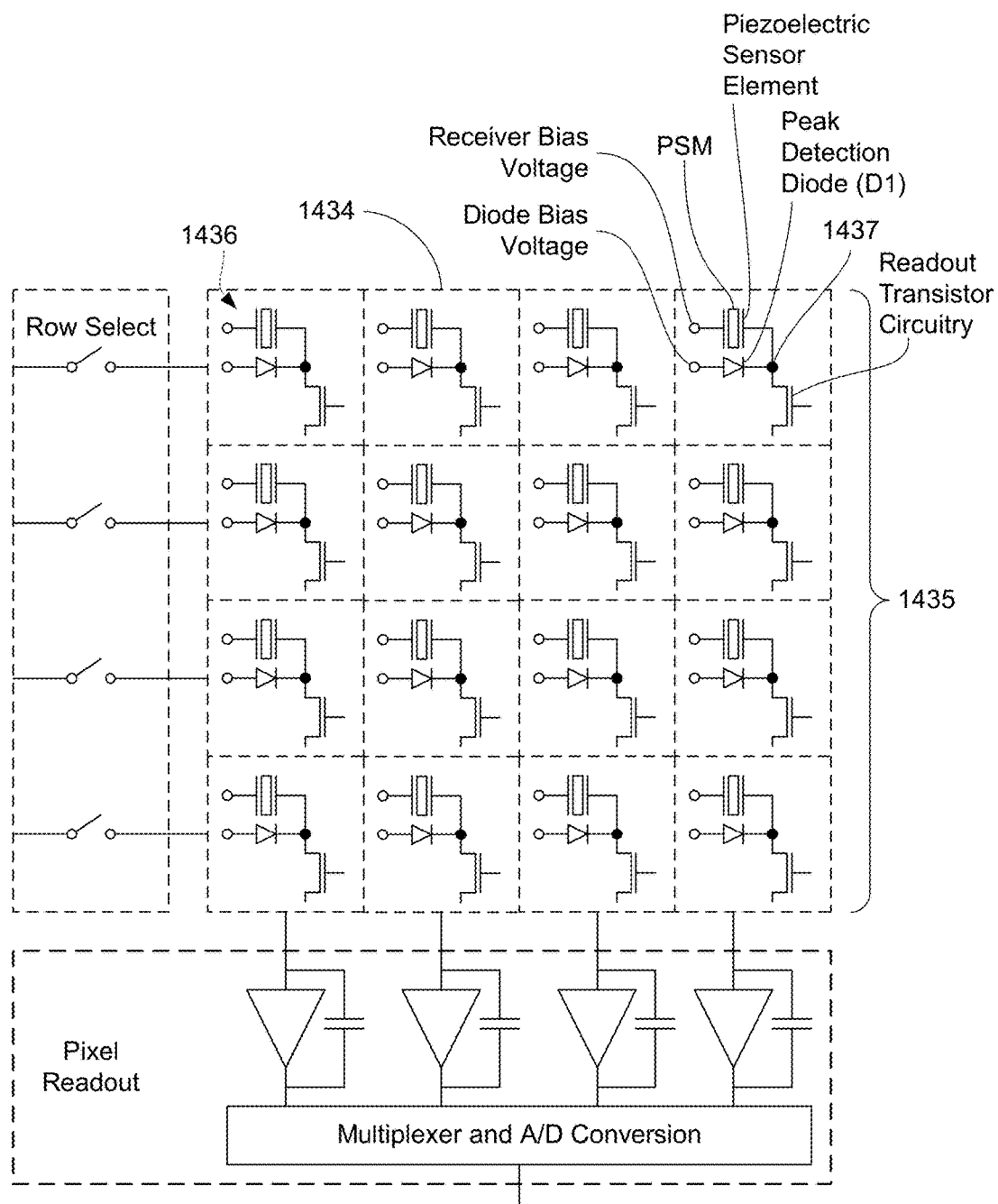
FIG. 14 representationally depicts aspects of a 4×4 pixel array of sensor pixels for an ultrasonic sensor system.

FIG. 14 representationally depicts aspects of a 4×4 pixel array of sensor pixels for an ultrasonic sensor system. Each pixel 1434 may be, for example, associated with a local region of piezoelectric sensor material (PSM), a peak detection diode (D1) and a readout transistor (M3); many or all of these elements may be formed on or in a substrate to form the pixel circuit 1436. In practice, the local region of piezoelectric sensor material of each pixel 1434 may transduce received ultrasonic energy into electrical charges. The peak detection diode D1 may register the maximum amount of charge detected by the local region of piezoelectric sensor material PSM. Each row of the pixel array 1435 may then be scanned, e.g., through a row select mechanism, a gate driver, or a shift register, and the readout transistor M3 for each column may be triggered to allow the magnitude of the peak charge for each pixel 1434 to be read by additional circuitry, e.g., a multiplexer and an A/D converter. The pixel circuit 1436 may include one or more TFTs to allow gating, addressing, and resetting of the pixel 1434.

Each pixel circuit 1436 may provide information about a small portion of the object detected by the ultrasonic sensor system. While, for convenience of illustration, the example shown in FIG. 14 is of a relatively coarse resolution, ultrasonic sensors having a resolution on the order of 500 pixels per inch or higher may be configured with an appropriately scaled structure. The detection area of the ultrasonic sensor system may be selected depending on the intended object of detection. For example, the detection area may range from about 5 mm×5 mm for a single finger to about 3 inches×3 inches for four fingers. Smaller and larger areas, including square, rectangular and non-rectangular geometries, may be used as appropriate for the target object.

Figure 15A:
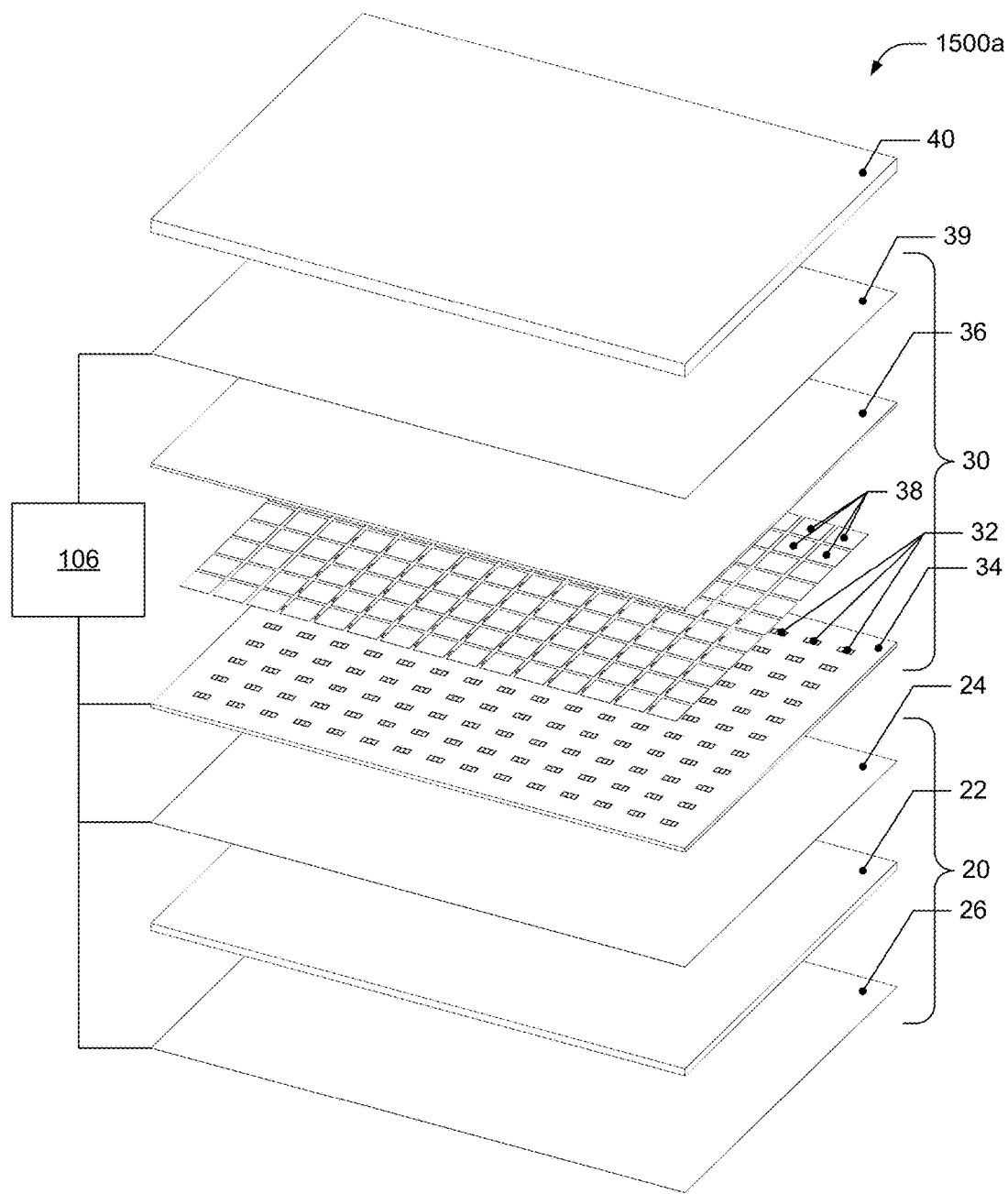
FIGS. 15A and 15B show example arrangements of ultrasonic transmitters and receivers in an ultrasonic sensor system, with other arrangements being possible.

FIG. 15A shows an example of an exploded view of an ultrasonic sensor system. In this example, the ultrasonic sensor system 1500a includes an ultrasonic transmitter 20 and an ultrasonic receiver 30 under a platen 40. According to some implementations, the ultrasonic receiver 30 may be an example of the ultrasonic sensor array 102 that is shown in FIG. 1B and described above. In some implementations, the ultrasonic transmitter 20 may be an example of the optional ultrasonic transmitter 108 that is shown in FIG. 1B and described above. The ultrasonic transmitter 20 may include a substantially planar piezoelectric transmitter layer 22 and may be capable of functioning as a plane wave generator. Ultrasonic waves may be generated by applying a voltage to the piezoelectric layer to expand or contract the layer, depending upon the signal applied, thereby generating a plane wave. In this example, the control system 106 may be capable of causing a voltage that may be applied to the planar piezoelectric transmitter layer 22 via a first transmitter electrode 24 and a second transmitter electrode 26. In this fashion, an ultrasonic wave may be made by changing the thickness of the layer via a piezoelectric effect. This ultrasonic wave may travel towards a finger (or other object to be detected), passing through the platen 40. A portion of the wave not absorbed or transmitted by the object to be detected may be reflected so as to pass back through the platen 40 and be received by at least a portion of the ultrasonic receiver 30. The first and second transmitter electrodes 24 and 26 may be metallized electrodes, for example, metal layers that coat opposing sides of the piezoelectric transmitter layer 22.

The ultrasonic receiver 30 may include an array of sensor pixel circuits 32 disposed on a substrate 34, which also may be referred to as a backplane, and a piezoelectric receiver layer 36. In some implementations, each sensor pixel circuit 32 may include one or more TFT elements, electrical interconnect traces and, in some implementations, one or more additional circuit elements such as diodes, capacitors, and the like. Each sensor pixel circuit 32 may be configured to convert an electric charge generated in the piezoelectric receiver layer 36 proximate to the pixel circuit into an electrical signal. Each sensor pixel circuit 32 may include a pixel input electrode 38 that electrically couples the piezoelectric receiver layer 36 to the sensor pixel circuit 32.

In the illustrated implementation, a receiver bias electrode 39 is disposed on a side of the piezoelectric receiver layer 36 proximal to platen 40. The receiver bias electrode 39 may be a metallized electrode and may be grounded or biased to control which signals may be passed to the array of sensor pixel circuits 32. Ultrasonic energy that is reflected from the exposed (top) surface of the platen 40 may be converted into localized electrical charges by the piezoelectric receiver layer 36. These localized charges may be collected by the pixel input electrodes 38 and passed on to the underlying sensor pixel circuits 32. The charges may be amplified or buffered by the sensor pixel circuits 32 and provided to the control system 106.

The control system 106 may be electrically connected (directly or indirectly) with the first transmitter electrode 24 and the second transmitter electrode 26, as well as with the receiver bias electrode 39 and the sensor pixel circuits 32 on the substrate 34. In some implementations, the control system 106 may operate substantially as described above. For example, the control system 106 may be capable of processing the amplified signals received from the sensor pixel circuits 32.

The control system 106 may be capable of controlling the ultrasonic transmitter 20 and/or the ultrasonic receiver 30 to obtain ultrasonic image data, e.g., by obtaining fingerprint images. Whether or not the ultrasonic sensor system 1500a includes an ultrasonic transmitter 20, the control system 106 may be capable of obtaining attribute information from the ultrasonic image data. In some examples, the control system 106 may be capable of controlling access to one or more devices based, at least in part, on the attribute information. The ultrasonic sensor system 1500a (or an associated device) may include a memory system that includes one or more memory devices. In some implementations, the control system 106 may include at least a portion of the memory system. The control system 106 may be capable of obtaining attribute information from ultrasonic image data and storing the attribute information in the memory system. In some implementations, the control system 106 may be capable of capturing a fingerprint image, obtaining attribute information from the fingerprint image and storing attribute information obtained from the fingerprint image (which may be referred to herein as fingerprint image information) in the memory system. According to some examples, the control system 106 may be capable of capturing a fingerprint image, obtaining attribute information from the fingerprint image and storing attribute information obtained from the fingerprint image even while maintaining the ultrasonic transmitter 20 in an "off" state.

In some implementations, the control system 106 may be capable of operating the ultrasonic sensor system 1500a in an ultrasonic imaging mode or a force-sensing mode. In some implementations, the control system may be capable of maintaining the ultrasonic transmitter 20 in an "off" state when operating the ultrasonic sensor system in a force-sensing mode. The ultrasonic receiver 30 may be capable of functioning as a force sensor when the ultrasonic sensor system 1500a is operating in the force-sensing mode. In some implementations, the control system 106 may be capable of controlling other devices, such as a display system, a communication system, etc. In some implementations, the control system 106 may be capable of operating the ultrasonic sensor system 1500a in a capacitive imaging mode.

The platen 40 may be any appropriate material that can be acoustically coupled to the receiver, with examples including plastic, ceramic, sapphire, metal and glass. In some implementations, the platen 40 may be a cover plate, e.g., a cover glass or a lens glass for a display. Particularly when the ultrasonic transmitter 20 is in use, fingerprint detection and imaging can be performed through relatively thick platens if desired, e.g., 3 mm and above. However, for implementations in which the ultrasonic receiver 30 is capable of imaging fingerprints in a force detection mode or a capacitance detection mode, a thinner and relatively more compliant platen 40 may be desirable. According to some such implementations, the platen 40 may include one or more polymers, such as one or more types of parylene, and may be substantially thinner. In some such implementations, the platen 40 may be tens of microns thick or even less than 10 microns thick.

Examples of piezoelectric materials that may be used to form the piezoelectric receiver layer 36 include piezoelectric polymers having appropriate acoustic properties, for example, an acoustic impedance between about 2.5 MRayls and 5 MRayls. Specific examples of piezoelectric materials that may be employed include ferroelectric polymers such as polyvinylidene fluoride (PVDF) and polyvinylidene fluoride-trifluoroethylene (PVDF-TrFE) copolymers. Examples of PVDF copolymers include 60:40 (molar percent) PVDF-TrFE, 70:30 PVDF-TrFE, 80:20 PVDF-TrFE, and 90:10 PVDR-TrFE. Other examples of piezoelectric materials that may be employed include polyvinylidene chloride (PVDC) homopolymers and copolymers, polytetrafluoroethylene (PTFE) homopolymers and copolymers, and diisopropylammonium bromide (DIPAB).

The thickness of each of the piezoelectric transmitter layer 22 and the piezoelectric receiver layer 36 may be selected so as to be suitable for generating and receiving ultrasonic waves. In one example, a PVDF planar piezoelectric transmitter layer 22 is approximately 28 µm thick and a PVDF-TrFE receiver layer 36 is approximately 12 µm thick. Example frequencies of the ultrasonic waves may be in the range of 5 MHz to 30 MHz, with wavelengths on the order of a millimeter or less.

Figure 15B:
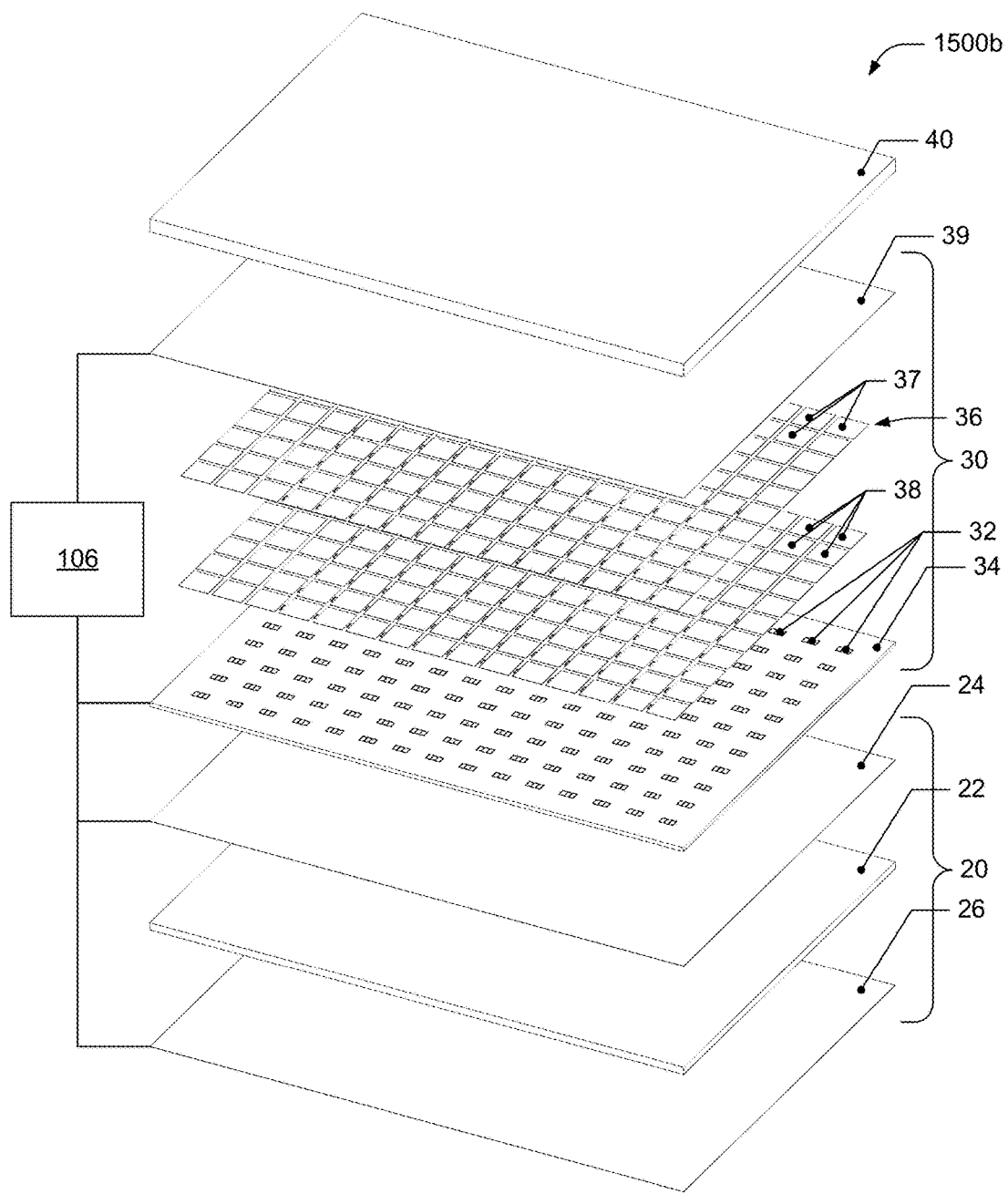

FIG. 15B shows an exploded view of an alternative example of an ultrasonic sensor system. In this example, the piezoelectric receiver layer 36 has been formed into discrete elements 37. In the implementation shown in FIG. 15B, each of the discrete elements 37 corresponds with a single pixel input electrode 38 and a single sensor pixel circuit 32. However, in alternative implementations of the ultrasonic sensor system 1500b, there is not necessarily a one-to-one correspondence between each of the discrete elements 37, a single pixel input electrode 38 and a single sensor pixel circuit 32. For example, in some implementations there may be multiple pixel input electrodes 38 and sensor pixel circuits 32 for a single discrete element 37.

FIGS. 15A and 15B show example arrangements of ultrasonic transmitters and receivers in an ultrasonic sensor system, with other arrangements being possible. For example, in some implementations, the ultrasonic transmitter 20 may be above the ultrasonic receiver 30 and therefore closer to the object(s) to be detected. In some implementations, the ultrasonic transmitter may be included with the ultrasonic sensor array (e.g., a single-layer transmitter and receiver). In some implementations, the ultrasonic sensor system may include an acoustic delay layer. For example, an acoustic delay layer may be incorporated into the ultrasonic sensor system between the ultrasonic transmitter 20 and the ultrasonic receiver 30. An acoustic delay layer may be employed to adjust the ultrasonic pulse timing, and at the same time electrically insulate the ultrasonic receiver 30 from the ultrasonic transmitter 20. The acoustic delay layer may have a substantially uniform thickness, with the material used for the delay layer and/or the thickness of the delay layer selected to provide a desired delay in the time for reflected ultrasonic energy to reach the ultrasonic receiver 30. In doing so, the range of time during which an energy pulse that carries information about the object by virtue of having been reflected by the object may be made to arrive at the ultrasonic receiver 30 during a time range when it is unlikely that energy reflected from other parts of the ultrasonic sensor system is arriving at the ultrasonic receiver 30. In some implementations, the substrate 34 and/or the platen 40 may serve as an acoustic delay layer.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

The invention claimed is:

1. An apparatus, comprising:
    an ultrasonic sensor array; and
    a control system, at least part of which is coupled to the ultrasonic sensor array, the control system configured to:
        acquire first image data, for an area of a finger, generated by the ultrasonic sensor array, the first image data corresponding to at least one first reflected ultrasonic wave received by at least a portion of the ultrasonic sensor array from a target object during a first acquisition time window;

acquire second image data, for the same area of the finger, generated by the ultrasonic sensor array, the second image data corresponding to at least one second reflected ultrasonic wave received by at least the portion of the ultrasonic sensor array from the target object during a second acquisition time window that is longer than the first acquisition time window; and initiate an authentication process based on the first image data and the second image data.

2. The apparatus of claim 1, wherein the first acquisition time window is initiated at an end time of a first acquisition time delay and wherein the second acquisition time window is initiated at an end time of a second acquisition time delay.

3. The apparatus of claim 2, wherein the first acquisition time delay and the second acquisition time delay are of equal duration.

4. The apparatus of claim 2, wherein the apparatus includes a platen positioned with respect to the ultrasonic sensor array and wherein the first acquisition time delay corresponds to an expected amount of time for an ultrasonic wave reflected from a surface of the platen to be received by at least a portion of the ultrasonic sensor array.

5. The apparatus of claim 2, wherein the first acquisition time delay and the first acquisition time window cause the first image data to correspond to a fingerprint feature of the target object.

6. The apparatus of claim 5, wherein the second acquisition time delay and the second acquisition time window cause the second image data to correspond to the fingerprint feature of the target object and to a sub-epidermal feature of the target object.

7. The apparatus of claim 1, wherein the target object comprises a user's finger, and at least a portion of the first image data represents at least one fingerprint feature of the user's finger, and at least a portion of the second image data represents at least one sub-epidermal feature of the user's finger.

8. The apparatus of claim 1, wherein the control system is further configured to acquire third image data generated by the ultrasonic sensor array, the third image data corresponding to at least one third reflected ultrasonic wave received by at least the portion of the ultrasonic sensor array from the target object, and wherein the initiated authentication process is based, at least in part, on identifying a temporal-based feature difference of the target object between the third image data and either the first image data or the second image data.

9. The apparatus of claim 8, wherein the initiated authentication process generates a liveness indicator based, at least in part, on the temporal-based feature difference of the target object.

10. The apparatus of claim 1, wherein the authentication process involves detecting one or more surface fingerprint features on a surface of the target object and one or more subsurface fingerprint features below the surface of the target object.

11. The apparatus of claim 10, wherein the initiated authentication process generates a spoof-detected indication based on differences between at least one of the one or more surface fingerprint features and at least one of the one or more subsurface fingerprint features.

12. The apparatus of claim 10, wherein the control system is further configured to store at least one of the first image data, the second image data, fingerprint minutiae, fingerprint keypoints or fingerprint features if surface fingerprint features and subsurface fingerprint features are detected.

13. The apparatus of claim 1, wherein, as part of the initiated authentication process, a fingerprint feature on a surface of the target object is identified based on an enrolled fingerprint template, and wherein the initiated authentication process is further based on a plurality of image data acquired in a sub-surface region of the target object based on the identified fingerprint feature.

14. The apparatus of claim 13, wherein the plurality of image data is generated by at least a portion of the ultrasonic sensor array.

15. The apparatus of claim 13, wherein a candidate user is validated based, at least in part, on the presence or absence of one or more temporal variations in the plurality of image data acquired in the sub-surface region.

16. An authentication method, comprising:
acquiring first image data, for an area of a finger, generated by an ultrasonic sensor array, the first image data corresponding to at least one first reflected ultrasonic wave received by at least a portion of the ultrasonic sensor array from a target object during a first acquisition time window;

acquiring second image data, for the same area of the finger, generated by the ultrasonic sensor array, the second image data corresponding to at least one second reflected ultrasonic wave received by at least a portion of the ultrasonic sensor array from the target object during a second acquisition time window that is longer than the first acquisition time window; and initiating an authentication process based on the first image data and the second image data.

17. The method of claim 16, wherein the first acquisition time window is initiated at an end time of a first acquisition time delay and wherein the second acquisition time window is initiated at an end time of a second acquisition time delay.

18. The method of claim 17, wherein the first acquisition time delay and the second acquisition time delay are of equal duration.

19. The method of claim 17, wherein the first acquisition time delay or the second acquisition time delay corresponds to an expected amount of time for an ultrasonic wave to be reflected from a surface of a platen to be received by the ultrasonic sensor array.

20. The method of claim 17, wherein the first acquisition time delay and the first acquisition time window cause the first image data to correspond to a fingerprint feature of the target object.

21. The method of claim 20, wherein the second acquisition time delay and the second acquisition time window cause the second image data to correspond to the fingerprint feature of the target object and to a sub-epidermal feature of the target object.

22. The method of claim 16, further comprising:
storing at least one of the first image data, the second image data, fingerprint minutiae, fingerprint keypoints or fingerprint features if surface fingerprint features on the surface of the target object and subsurface fingerprint features below the surface of the target object are detected.

23. A non-transitory medium having software stored thereon, the software including instructions for controlling one or more devices to perform an authentication method, the method comprising:
acquiring first image data generated by an ultrasonic sensor array, the first image data corresponding to at least one first reflected ultrasonic wave received by at least a portion of the ultrasonic sensor array from a target object during a first acquisition time window;
acquiring second image data generated by the ultrasonic sensor array, the second image data corresponding to at least one second reflected ultrasonic wave received by at least a portion of the ultrasonic sensor array from the target object during a second acquisition time window that is longer than the first acquisition time window; and
initiating an authentication process based on the first image data and the second image data.

24. The non-transitory medium of claim 23, wherein the first acquisition time window is initiated at an end time of a first acquisition time delay and wherein the second acquisition time window is initiated at an end time of a second acquisition time delay.

25. The non-transitory medium of claim 24, wherein the first acquisition time delay and the second acquisition time delay are of equal duration.

26. The non-transitory medium of claim 24, wherein the first acquisition time delay or the second acquisition time delay corresponds to an expected amount of time for an ultrasonic wave reflected from a surface of a platen to be received by the ultrasonic sensor array.

27. The non-transitory medium of claim 24, wherein the first acquisition time delay and the first acquisition time window cause the first image data to correspond to a fingerprint feature of the target object.

28. The non-transitory medium of claim 27, wherein the second acquisition time delay and the second acquisition time window cause the second image data to correspond to the fingerprint feature of the target object and to a sub-epidermal feature of the target object.

29. The non-transitory medium of claim 23, the method further comprising:
storing at least one of the first image data, the second image data, fingerprint minutiae, fingerprint keypoints or fingerprint features if surface fingerprint features on the surface of the target object and subsurface fingerprint features below the surface of the target object are detected.

30. An apparatus, comprising:
an ultrasonic sensor array; and
a control system, at least part of which is coupled to the ultrasonic sensor array, the control system configured to:
control the ultrasonic sensor array to acquire ultrasonic image data corresponding to at least one reflected ultrasonic wave received by at least a portion of the ultrasonic sensor array from a target object during an acquisition time window;
extract first fingerprint data, for an area of a finger, from the ultrasonic image data, the first fingerprint data corresponding to a first fingerprint;
determine whether the ultrasonic image data includes second fingerprint data, for the same area of the finger, corresponding to a second fingerprint that is different from the first fingerprint; and, upon determining that the ultrasonic image data does not include second fingerprint data corresponding to a second fingerprint that is different from the first fingerprint, perform an authentication process based, at least in part, on the first fingerprint data.

31. The apparatus of claim 30, wherein the control system is further configured to determine sub-epidermal features from the ultrasonic image data and wherein the authentication process is based, at least in part, on the sub-epidermal features.

32. The apparatus of claim 30, wherein the control system is further configured to:
obtain first sub-epidermal features from first ultrasonic image data at a first time;
obtain second sub-epidermal features from second ultrasonic image data at a second time; and
make a liveness determination based on a change between the first sub-epidermal features and the second sub-epidermal features.

33. The apparatus of claim 30, wherein, upon determining that that the ultrasonic image data includes the second fingerprint data, the control system is further configured to:
store the ultrasonic image data, the first fingerprint data, or the second fingerprint data or combination thereof.

34. An authentication method, comprising:
controlling an ultrasonic sensor array to acquire ultrasonic image data corresponding to at least one reflected ultrasonic wave received by at least a portion of the ultrasonic sensor array from a target object during an acquisition time window;
extracting first fingerprint data, for an area of a finger, from the ultrasonic image data, the first fingerprint data corresponding to a first fingerprint;
determining whether the ultrasonic image data includes second fingerprint data for the same area of the finger, corresponding to a second fingerprint that is different from the first fingerprint; and, upon determining that the ultrasonic image data does not include second fingerprint data corresponding to a second fingerprint that is different from the first fingerprint,
performing an authentication process based, at least in part, on the first fingerprint data.

35. The method of claim 34, further comprising determining sub-epidermal features from the ultrasonic image data, and wherein the authentication process is based, at least in part, on the sub-epidermal features.

36. The method of claim 34, further comprising:
obtaining first sub-epidermal features from first ultrasonic image data at a first time;
obtaining second sub-epidermal features from second ultrasonic image data at a second time; and
making a liveness determination based on a change between the first sub-epidermal features and the second sub-epidermal features.

37. The method of claim 34, wherein the method further comprises:
storing the ultrasonic image data or the first fingerprint data or combination thereof.

38. A non-transitory medium having software stored thereon, the software including instructions for controlling one or more devices to perform an authentication method, the method comprising:
controlling an ultrasonic sensor array to acquire ultrasonic image data corresponding to at least one reflected ultrasonic wave received by at least a portion of the ultrasonic sensor array from a target object during an acquisition time window;
extracting first fingerprint data, for an area of a finger, from the ultrasonic image data, the first fingerprint data corresponding to a first fingerprint;
determining whether the ultrasonic image data includes second fingerprint data, for the same area of the finger, corresponding to a second fingerprint that is different from the first fingerprint; and, upon determining that the ultrasonic image data does not include second fingerprint data corresponding to a second fingerprint that is different from the first fingerprint, performing an authentication process based, at least in part, on the first fingerprint data.

39. The non-transitory medium of claim 38, wherein the method further comprises determining sub-epidermal features from the ultrasonic image data, and wherein the authentication process is based, at least in part, on the sub-epidermal features.

40. The non-transitory medium of claim 38, wherein the method further comprises:

obtaining first sub-epidermal features from first ultrasonic image data at a first time;

obtaining second sub-epidermal features from second ultrasonic image data at a second time; and making a liveness determination based on a change between the first sub-epidermal features and the second sub-epidermal features.

41. The non-transitory medium of claim 38 wherein, upon determining that that the ultrasonic image data includes the second fingerprint data, the method further comprises:

storing the ultrasonic image data, the first fingerprint data, or the second fingerprint data or combination thereof.

* * * * *